US012226250B2

(12) United States Patent
Wilson et al.

(10) Patent No.: US 12,226,250 B2
(45) Date of Patent: Feb. 18, 2025

(54) MULTIPLE MODALITY BODY COMPOSITION ANALYSIS

(71) Applicants: HOLOGIC, INC., Marlborough, MA (US); THE REGENTS OF THE UNIVERSITY OF CALIFORNIA, Oakland, CA (US)

(72) Inventors: Kevin E. Wilson, Marlborough, MA (US); John A. Shepherd, Oakland, CA (US); Bennett K. Ng, Oakland, CA (US); Mark Guetersloh, Marlborough, CA (US); Chao Huang, Marlborough, MA (US); Thomas L. Kelly, Marlborough, MA (US); Wei Wang, Marlborough, MA (US); Howard Weiss, Marlborough, MA (US)

(73) Assignees: Hologic, Inc., Marlborough, MA (US); The Regents of the University of California, Oakland, CA (US)

( * ) Notice: Subject to any disclaimer, the term of this patent is extended or adjusted under 35 U.S.C. 154(b) by 935 days.

(21) Appl. No.: 16/498,631

(22) PCT Filed: Mar. 22, 2018

(86) PCT No.: PCT/US2018/023817
§ 371 (c)(1),
(2) Date: Sep. 27, 2019

(87) PCT Pub. No.: WO2018/183086
PCT Pub. Date: Oct. 4, 2018

(65) Prior Publication Data
US 2020/0029927 A1     Jan. 30, 2020

Related U.S. Application Data

(60) Provisional application No. 62/480,017, filed on Mar. 31, 2017.

(51) Int. Cl.
A61B 6/00     (2024.01)
A61B 5/00     (2006.01)
(Continued)

(52) U.S. Cl.
CPC .......... *A61B 6/5247* (2013.01); *A61B 5/0064* (2013.01); *A61B 5/0077* (2013.01);
(Continued)

(58) Field of Classification Search
CPC .................................................. A61B 6/5247
See application file for complete search history.

(56) References Cited

U.S. PATENT DOCUMENTS 4,811,373 A     3/1989   Stein
4,831,527 A     5/1989   Clark
(Continued)

FOREIGN PATENT DOCUMENTS

CN     1767788      5/2006
CN     202723867    2/2013
(Continued)

OTHER PUBLICATIONS

Malkov et al. ( "Combining 3D optical imaging and dual energy absorptiometry to measure three compositional components" Proc SPIE Int Soc Opt Eng., Feb. 2014) (Year: 2014).*
(Continued)

*Primary Examiner* — Joseph M Santos Rodriguez
(74) *Attorney, Agent, or Firm* — Merchant & Gould P.C.

(57) ABSTRACT

Systems and methods for determining body composition by combining dual-energy x-ray (DXA) technology with three-dimensional (3D) optical technology and/or bioimpedance technology. A multi-modality scanning system may include a dual-energy x-ray source and an x-ray detector mounted to opposing sides a c-arm and configured to scan a patient on a optically translucent table. The system may also include
(Continued)

one or more 3D optical imaging devices to capture 3D optical images of the patient substantially concurrently with the emission of the dual energy x-rays. A bioimpedance machine may also be included in the multi-modality scanning system. Data based on the dual-energy x-rays may be combined with the data from the 3D optical images and/or the bioimpedance data to generate values of at least three compartments selected from: bone, fat tissue, lean tissue, dehydrated lean tissue, and water.

18 Claims, 14 Drawing Sheets

(51) Int. Cl.
    *A61B 5/107*     (2006.01)
    *A61B 6/04*     (2006.01)
    *A61B 6/50*     (2024.01)
    *G01G 19/44*     (2006.01)

(52) U.S. Cl.
    CPC .......... *A61B 5/1075* (2013.01); *A61B 5/1079* (2013.01); *A61B 5/4872* (2013.01); *A61B 5/4875* (2013.01); *A61B 6/0407* (2013.01); *A61B 6/4452* (2013.01); *A61B 6/482* (2013.01); *A61B 6/505* (2013.01); *G01G 19/445* (2013.01)

(56) References Cited

U.S. PATENT DOCUMENTS

| | | |
|---|---|---|
| 4,947,414 A | 8/1990 | Stein et al. |
| 4,980,904 A | 12/1990 | Sones et al. |
| 5,040,199 A | 8/1991 | Stein |
| 5,305,368 A | 4/1994 | Bisek et al. |
| 5,335,260 A | 8/1994 | Arnold |
| 5,771,272 A * | 6/1998 | Berger ............... A61B 6/505 378/207 |
| 5,778,045 A | 7/1998 | von Stetten |
| 5,949,846 A * | 9/1999 | Stein ............... A61B 6/505 378/54 |
| 6,081,582 A | 6/2000 | Mazess |
| 6,102,567 A | 8/2000 | Cabral |
| 6,160,866 A | 12/2000 | Mazess |
| 6,173,034 B1 | 1/2001 | Chao |
| 6,198,797 B1 | 3/2001 | Majima et al. |
| 6,215,846 B1 | 4/2001 | Mazess |
| 6,233,473 B1 | 5/2001 | Shepherd |
| 6,315,447 B1 | 11/2001 | Nord |
| 6,468,209 B1 | 10/2002 | Heymsfield |
| 6,816,564 B2 | 11/2004 | Charles, Jr. |
| 6,969,350 B1 | 11/2005 | Hawthorne |
| 6,999,549 B2 | 2/2006 | Sabol et al. |
| 7,198,404 B2 * | 4/2007 | Navab ............... A61B 6/4417 378/63 |
| 7,444,961 B1 | 11/2008 | Ellis |
| 7,595,043 B2 | 9/2009 | Hedrick |
| 7,725,153 B2 | 5/2010 | Kelly et al. |
| 7,801,350 B2 | 9/2010 | L Bras et al. |
| 8,300,911 B1 | 10/2012 | Payne et al. |
| 8,483,458 B2 | 7/2013 | Payne et al. |
| 8,634,629 B2 | 1/2014 | Wilson |
| 8,792,689 B2 | 7/2014 | Kelly et al. |
| 9,086,356 B1 | 7/2015 | Kelly et al. |
| 9,179,873 B2 | 11/2015 | Kelly et al. |
| 9,504,406 B2 | 11/2016 | Chetham et al. |
| 9,642,585 B2 | 5/2017 | Wilson |
| 9,865,050 B2 | 1/2018 | Kelly et al. |
| 10,390,784 B2 | 8/2019 | Wilson |
| 10,470,705 B2 | 11/2019 | Kelly |
| 10,499,865 B2 | 12/2019 | Wilson et al. |
| 10,515,451 B2 | 12/2019 | Kelly |
| 10,646,159 B2 | 5/2020 | Kelly |
| 11,701,079 B2 | 7/2023 | Wilson |
| 2001/0053202 A1 | 12/2001 | Mazess |
| 2002/0070365 A1 | 6/2002 | Karellas |
| 2004/0077088 A1 | 4/2004 | Charles, Jr. et al. |
| 2004/0101086 A1 | 5/2004 | Sabol et al. |
| 2004/0247076 A1 * | 12/2004 | Navab ............... A61B 5/0059 378/63 |
| 2005/0010106 A1 | 1/2005 | Lang et al. |
| 2005/0215882 A1 | 9/2005 | Chenevert |
| 2006/0074288 A1 | 4/2006 | Kelly et al. |
| 2007/0223795 A1 | 9/2007 | Qing et al. |
| 2007/0238957 A1 | 10/2007 | Yared |
| 2009/0279672 A1 | 11/2009 | Reiner |
| 2010/0081960 A1 * | 4/2010 | McKenna ............ A61B 5/4869 600/547 |
| 2010/0086185 A1 | 4/2010 | Weiss |
| 2010/0168530 A1 | 7/2010 | Chetham |
| 2010/0168551 A1 | 7/2010 | Moeller |
| 2010/0234719 A1 | 9/2010 | Kelly et al. |
| 2011/0002522 A1 | 1/2011 | Goto |
| 2011/0058725 A1 | 3/2011 | Markwardt et al. |
| 2011/0158386 A1 | 6/2011 | Payne et al. |
| 2011/0164798 A1 | 7/2011 | Masumoto |
| 2011/0235886 A1 | 9/2011 | Kelly et al. |
| 2011/0311122 A1 | 12/2011 | Kelly |
| 2012/0004570 A1 | 1/2012 | Shimizu |
| 2013/0051523 A1 | 2/2013 | Davydov et al. |
| 2013/0121461 A1 | 5/2013 | Toll |
| 2013/0308752 A1 | 11/2013 | Wilson |
| 2014/0288420 A1 * | 9/2014 | Goossen ............... A61B 6/5217 600/427 |
| 2014/0371570 A1 | 12/2014 | Davis et al. |
| 2015/0036910 A1 | 2/2015 | Kelly et al. |
| 2015/0146851 A1 | 5/2015 | Wilson |
| 2015/0374291 A1 | 12/2015 | Kelly et al. |
| 2016/0228057 A1 | 8/2016 | Kelly et al. |
| 2017/0046837 A1 | 2/2017 | Leinhard et al. |
| 2017/0135655 A1 | 5/2017 | Wang et al. |
| 2018/0021001 A1 | 1/2018 | Wilson |
| 2018/0049710 A1 | 2/2018 | Wilson |
| 2018/0189948 A1 | 7/2018 | Kelly |
| 2019/0059829 A1 | 2/2019 | Han |
| 2019/0102877 A1 | 4/2019 | Payne et al. |
| 2020/0046307 A1 | 2/2020 | Wilson |
| 2020/0060636 A1 | 2/2020 | Wilson |
| 2020/0167921 A1 | 5/2020 | Kelly |
| 2021/0052243 A1 | 2/2021 | Don et al. |
| 2021/0150704 A1 | 5/2021 | Bruening et al. |
| 2021/0361251 A1 | 11/2021 | Wilson |
| 2022/0225957 A1 | 7/2022 | Kelly |

FOREIGN PATENT DOCUMENTS

| | | |
|---|---|---|
| DE | 10 20120 204429 | 9/2013 |
| EP | 0747008 | 12/1996 |
| EP | 1882447 | 1/2008 |
| JP | H04-263842 | 9/1992 |
| JP | H09108206 | 4/1997 |
| JP | H10-151127 | 6/1998 |
| JP | 2004-081394 | 3/2004 |
| JP | 2007-524438 | 8/2007 |
| JP | 2010-042129 | 2/2010 |
| JP | 2010-57953 | 3/2010 |
| JP | 2010-510835 | 4/2010 |
| JP | 2010-253049 | 11/2010 |
| JP | 2010-253106 | 11/2010 |
| JP | 2011024773 | 2/2011 |
| JP | 2013-516706 | 5/2013 |
| JP | 6047347 | 12/2016 |
| JP | 2018506385 | 3/2018 |
| KR | 2018-0038251 | 4/2018 |
| WO | 2003052398 | 6/2003 |
| WO | 2010/051600 | 5/2010 |
| WO | 2010/095709 | 8/2012 |
| WO | 2014/066906 | 5/2014 |
| WO | 2016/138262 | 9/2016 |
| WO | 2016/177798 | 11/2016 |

(56) References Cited

FOREIGN PATENT DOCUMENTS

| WO | WO-2017055352 A1 * | 4/2017 | ............ A61B 5/0035 |
|---|---|---|---|
| WO | 2018192909 | 10/2018 | |

OTHER PUBLICATIONS

International Search Report and Written Opinion of the International Searching Authority for International Patent Application No. PCT/US2018/023817 mailed Sep. 4, 2018, 15 pages.
Malkov, S. et al., "Combining 3D optical imaging and dual energy absorptiometry to measure three compositional components", Progress in Biomedical Optics and Imaging, SPIE—International society for Optical Engineering, 8937: 893714-1-893714-6 (2014).
Michael et al., "Monte Carlo modelling of an extended DXA technique", Physics in Medicine and Biology, vol. 43, No. 9, Sep. 1, 1998, pp. 2583-2596.
European Communication in Application 18716810.9, mailed Nov. 10, 2020, 9 pages.
PCT International Preliminary Report and on Patentability in International Application PCT/US2018/023817, mailed Oct. 1, 2019, 7 pages.
Yamada, Yosuke, The appraisal method of Yosuke, and the amount of skeletal muscle and muscular power, medical development, Mar. 1, 2014, vol. 248, No. 9, pp. 670-678, with an English translation summary.
Chan, "Performance of Dual-Energy X-ray Absorptiometry in Evaluating Bone, Lean Body Mass, and Fat in Pediatric Subjects", Journal of Bone and Mineral Research, vol. 7 (Year 1992), 7 pgs.
De Lorenzo, A. et al., "Predicting body cell mass with bioimpedance by using theoretical methods: a technological review", J. Appl. Physiol 1997; 82: 1542-58.
Lehmann et al., "Generalized Image Combinations in Dual KVP Digital Radiography", Med. Phys. 8(5) Sep./Oct. 1981, 9 pgs.
Lustgarten, M.S. et al., "Assessment of Analytical Methods Used to Measure Changes in Body Composition in the Elderly and Recommendations for Their Use in Phase II Clinical Trials", J. Nutr. Health Aging, 15(5): 368-375 (2011).
McKiernan F.E., et al. "A long femur scan field does not alter proximal femur bone mineral density measurements by dual-energy X-ray absorptiometry." J Clin Densitom. Jul.-Sep. 2011;14(3):354-8.
PCT International Preliminary Report on Patentability in International Application PCT/US2016/019562, dated Aug. 29, 2017, 8 pgs.
PCT International Search Report and Written Opinion in International Application PCT/US2016/019562, mailed Jul. 21, 2016, 15 pages.
Pietrobelli, A. et al., "Dual-energy X-ray absorptiometry: fat estimation errors due to variation in soft tissue hydration", The American Physiological Society, E808-E816 (1998).
Prado, C. et al., "Lean Tissue Imaging: A New Era for Nutritional Assessment and Intervention", Journal of Parental and Enteral Nutrition, 38(8): 940-953 (2014).
Sayer, A.A. et al., "New horizons in the pathogenesis, diagnosis and management of sarcopenia", Age and Ageing, 42: 145-150 (2013).
Shane, E., et al. "Atypical subtrochanteric and diaphyseal femoral fractures: report of a task force of the American Society for Bone and Mineral Research." J Bone Miner Res. Nov. 2010;25(11):2267-94.
Shane, E., et al."Atypical subtrochanteric and diaphyseal femoral fractures: Second report of a task force of the American society for bone and mineral research." J Bone Miner Res. May 28, 2013. doi: 10.1002/jbmr.1998. [Epub ahead of print], pp. 1-23.
Sorenson, J.A. et al., "Simulation of dual-energy x-ray absorptiometry", Medical Physics, 16(1): 75-80 (1989).
Wear, J. et al., "CZT detector for dual-energy x-ray absorptiometry (DEXA)", Proceedings of SPIE, 4142: 175-188 (2000).

WHO publication—Kanis JA, on behalf of the World Health Organisation Scientific Group, "Assessment of osteoporosis at the primary health care level", WHO Collaborating Centre for Metabolic Bone Diseases, University of Sheffield 2007, 339 pgs.
Wilson, J.P et al., "Improved 4-Compartment body-composition model for a clinically accessible measure of total body protein", Am J Clin Nutr. 2013; 97: 497-504.
Wilson, J.P. et al., "Dual-Energy X-Ray absorpitometry-based body volume measurement for 4-compartment body composition", The American Journal of Clinical Nutrition, 2012; 95 (1): 25-31.
Bertin et al., "Measurement of visceral adipose tissue by DXA combined with anthropometry in obese humans," Int J Obes Relat Metab Disord., 24(3):263-270 (Mar. 2000).
Gronenmeyer et al., "Fast Adipose Tissue (FAT) Assessment by MRI," Magnetic Resonance Imaging, 18:815-818 (2000).
Hayashi et al., "Visceral Adiposity and the Prevalence of Hypertension in Japanese Americans, " Circulation, 108:1718-1723 (2003).
Hill et al., "Estimating Abdominal Adipose Tissue With DXA and Anthropometry," Obesity, 15(2):504-510 (Feb. 2007).
Hologic Clarity of Vision, Discovery QDR Series Advanced Point-of-Care Bone Health Assessment, Hologic Osteoporosis Assessment (May 2004), 13 pages.
Hologic Clarity of Vision, Explorer Fan-Beam DXA for the Cost-Conscious Practice, Hologic Osteoporosis Assessment (Jan. 2004), 11 pages.
Jensen et al., "Measurement of abdominal and visceral fat with computed tomography and dual-energy x-ray absorptiometry," Am J Clin Nutr., 61(2):274-278 (Feb. 1995).
Kamel et al., "Usefulness of Anthropometry and DXA in Predicting Intra-abdominal Fat in Obese Men and Women," Obesity Research, 8(1) 36-42 (2000).
Kelly et al., "DXA Body Composition: Theory and Practice," Appl Radia., 49(5:6):511-513 (1988).
Kobayashi et al., "A novel method of measuring intra-abdominal fat vol. using helical computed tomography," International Journal of Obesity, 26:398-402 (2002).
Krotkiewski et al., "Impact of Obesity on Metabolism in Men and Women. Importance of Regional Adipose Tissue Distribution," J Clin Invest., The American Society for Clinical Investigation, Inc., 72:1150-1162 (1983).
Kvist et al., "Total and visceral adipose-tissue volumes derived from measurements with computed tomography in adult men and women: predictive equations 1-3," Am J Clin Nutr, 48:1351-1361 (1988).
Ley, "Sex- and menopause-associated changes in body-fat distribution," Am J Clin Nut, 55:950-954 (1993).
Montague et al., "Perspectives in Diabetes the Perils of Portliness Causes and Consequences of Visceral Adiposity," Diabetes, 49:883-888 (2000).
Morricone et al., "Relationship of Visceral Fat Distribution to Angiographically Assessed Coronary Artery Disease: Results in Subjects With or Without Diabetes or Impaired Glucose Tolerance," PMID: 12616807 [PubMed—indexed for Medline], Nutr Metab Cardiovasc Dis., 12(5):275-283 (2002).
Nicklas et al., "Visceral Adipose Tissue Cutoffs Associated With Metabolic Risk Factors for Coronary Heart Disease in Women," Epidemiology/Health Services/Psychosocial Research, Diabetes Care, 26:1413-1420 (May 2003).
Pritchard et al., "Evaluation of Dual Energy X-Ray Absorptiometry as a Method of Measurement of Body Fat," European Journal of Clinical Nutrition, 47:216-228 (1993).
Slosman et al., "Assessment of Whole-Body Composition With Dual-Energy X-Ray Absorptiometry," Radiology, 185:593-598 (1992).
Trueth et al., "Estimating Intraabdominal Adipose Tissue in Women by Dual-Energy X-Ray Absorptiometry," Am J Clin Nutr, 62:427-432 (1995).
Sanada et al., "A cross-sectional study of sarcopenia in Japanese men and women: Reference values and association with cardiovascular risk factors", European Journal of Applied Physiology 110(1): 57-65, Sep. 2010.

(56) References Cited

OTHER PUBLICATIONS

Chan-Shien, Ho, et al., "Application of deep learning neural network in predicting bone mineral density from plain X-ray radiography", Archives of Osteoporosis, Springer, London, vol. 16, No. 1, Oct. 9, 2021, 12 pages.

De Souza, Joao et al., "Predicting body measures from 2D images using Convolutional Neural Networks", 2020 International Joint Conference on Neural Networks (IJCNN), IEEE, Jul. 19, 2020, pp. 1-6.

Miccini, Riccardo et al., "HRTF Individualization using Deep Learning", 2020 IEEE Conference on Virtual Reality and 3D User Interfaces Abstracts and Workshops (VRW), IEEE, Mar. 22, 2020, pp. 390-395.

International Search Report for PCT/US2022/080252, dated Mar. 10, 2023 (19 pages).

Stein et al., "A Dual-Energy X-Ray Bone Densitometer incorporating an internal reference systems", Workshop on Non-Invasive Bone Measurements, Leuven, Belgium, Sep. 1987, 26 pages.

Author Unknown, "National Health and Nutrition Examination Survey (NHANES): Dual Energy Xray Absorptiometry (DXA) Procedures Manual", CDC, Jan. 2017, 115 pages.

Tan et al., "Sarcopenia in an Overweight or Obese Patient is an Adverse Prognostic Factor in Pancreatic Cancer", Xlin Cancer Res 2009; 15(22), Nov. 15, 2009, pp. 6973-6979.

European Communication in Application 24193308.4, mailed Sep. 24, 2024, 8 pages.

Hayes et al., "DXA: Potential for Creating a Metabolic Map of Organ-Tissue Resting Energy Expenditure Components", Obesity Research vol. 10, No. 10, Oct. 2002, pp. 969-977.

Ho, Chan-Shien et al., "Application of deep learning neural network in predicting bone mineral density from plain X-ray radiography", Archives of Osteoporosis, Springer London, vol. 16, No. 1, Oct. 9, 2021, 12 pgs.

Rafael do Espirit Santo, "Principal Component Analysis applied to Digital Image Compression", Einstein (Sao Paulo) 10 (2), Jun. 2012 (available at https://doi.ord/10.1590S1679-45082012000200004), pp. 135-139.

Zimmermann et al., "Detection of overweight and obesity in a national sample of 6-12 year old Swiss children: accuracy and validity of reference values for body mass index from the US Centers for Disease Control and Prevention and the International Obesity Task Force", 2010, Am J Clin Nutr 2004; 79; 838-43.

\* cited by examiner

MULTIPLE MODALITY BODY COMPOSITION ANALYSIS

CROSS-REFERENCE TO RELATED APPLICATIONS

This application is a National Stage Application of PCT/US2018/023817, filed Mar. 22, 2018, which claims priority to U.S. Provisional Patent Application No. 62/480,017, filed Mar. 31, 2017, the disclosures of which are hereby incorporated by reference herein in their entireties. To the extent appropriate, a claim of priority is made to each of the above disclosed applications.

INTRODUCTION

Understanding the body composition of a patient can be an important aspect in diagnosing health issues and providing health-related guidance. For example, as the population of older Americans, defined as persons aged 65 and older, grows in proportion to the total US population, it is increasingly important to better understand, diagnose, and treat complex age-related syndromes that affect this subset of the US population. In addition, as competition continues to increase amongst athletes, development of effective and efficient training programs to improve performance are also important.

Body composition systems and methods, however, have previously been limited in their accuracy and usefulness in diagnosing such systems and evaluating performance regimes. For instance, dual-energy x-ray absorptiometry (DXA) machines, also known as densitometers, have been commonly used to determine the bone density of patient. Bone density measurements are useful for determining ailments such as osteoporosis, but may have more limited value in assessing other syndromes or assessing physical performance gains made by a particular training regimen. Further, DXA machines fundamentally cannot resolve more than two tissue types at a given pixel, so several assumptions must be made when measuring body composition using DXA. Those assumptions may lead to some potential inaccuracies. Also, by being able to only resolve two tissue types, the usefulness in determining other types of syndromes or performance improvements are inherently limited.

SUMMARY

In one aspect, the technology relates to a system for determining body composition, the system including: a support arm; a dual-energy x-ray source mounted to the support arm, the dual energy x-ray source configured to emit dual-energy x-rays towards the scanning target; an x-ray detector mounted to the support arm and configured to detect the dual-energy x-rays emitted from the dual-energy x-ray source after passing through the scanning target; and a first 3D optical imaging device mounted to the support arm and configured to obtain a 3D optical image of a first side of the scanning target substantially concurrently with the emission of the dual-energy x-rays. In an example, the system includes an optically translucent patient support table on which the scanning target is positioned, wherein the optically translucent table is disposed between the dual energy x-ray source and the detector. In another example, the support arm is configured to move along a longitudinal axis of the scanning target. In yet another example, the support arm has an upper arm and a lower arm, the upper arm and lower arm disposed on opposite sides of a scanning target; the first 3D optical imaging device is mounted to the upper arm; and the system further includes a second 3D optical imaging device, mounted to the lower arm, to optically scan a second side of the scanning target substantially concurrently with the emission of dual-energy x-rays. In still another example, the first 3D optical imaging device is selected from a group consisting of a stereoscopic device, a laser scanning device, a structured light device, and a modulated light device.

In another example of the above aspect, the system includes processing device, wherein the x-ray detector and the first 3D optical imaging device are communicatively coupled to the processing device, and wherein the processing device is configured to compute the thickness of the scanning target on a per pixel basis. In an example, the processing device is further configured to determine, on a per-pixel basis, values of at least three compartments selected from: bone, fat tissue, lean tissue, dehydrated lean tissue, and water. In another example, the system includes a bioimpedance machine mounted to a portion of the system and communicatively coupled to the processing device. In yet another example, the system is configured to scan a patient in a standing position. In still another example, the system includes a scale.

In another example of the above aspect, the system includes a scale operatively connected to the table and configured to detect a weight of the scanning target. In an example, the table includes a scale in each of the legs of the table. In another example, the x-ray source is configured to move along the support arm is a direction transverse to the longitudinal axis of the patient.

In another aspect, the technology relates to a system for determining body composition, the system including: a support arm; a dual-energy x-ray source mounted to the support arm, the dual energy x-ray source configured to emit dual-energy x-rays towards a scanning target; an x-ray detector mounted to the support arm and configured to detect the dual-energy x-rays emitted from the dual-energy x-ray source after passing through the scanning target; and a bioimpedance machine operatively connected to a portion of the system and configured to perform bioimpedance analysis on at least one portion of the scanning target. In an example, the system includes a patient support table on which the scanning target is located during scanning, wherein the patient support table is in between the dual energy x-ray source and the detector. In another example, the support arm is configured to move together along a longitudinal axis of the scanning target. In yet another example, the system includes a plurality of 3D optical imaging devices mounted to the support arm, wherein the plurality of 3D optical imaging devices are configured to image the scanning target substantially concurrently with the emission of the dual-energy x-rays. In still another example, the bioimpedance machine determines an amount of water in the at least one portion of the scanning target.

In another example of the above aspect, the system includes a processing device configured to determine a value of at least three compartments selected from: bone, fat tissue, lean tissue, dehydrated lean tissue, and water, for the at least one segment of the scanning target. In an example, the system is configured to scan a patient in a standing position. In another example, the at least one portion includes an appendage of the scanning target.

In another aspect, the technology relates to a method for determining a composition of a scanning target, the method including: moving a dual-energy x-ray source, an x-ray detector, and at least one 3D optical imaging device along a scan path of the scanning target; emitting dual-energy x-rays from the x-ray source; detecting the dual-energy x-rays after the dual-energy x-rays have passed through the scanning target; capturing, substantially concurrently with the emission of the dual-energy x-rays, 3D optical images of the scanning target; based on the captured 3D optical images, determining a thickness of the scanning target on a pixel-by-pixel basis; and determining, by a processor, based on the thickness of the scanning target and the captured dual-energy x-rays, a value of at least three compartments selected from: bone, fat tissue, lean tissue, dehydrated lean tissue, and water, for at least one pixel. In an example, determining the thickness of the of the scanning target further includes: estimating a trajectory of an x-ray traveling from the dual-energy x-ray source to a predetermined pixel for which the thickness is being calculated; and based on the captured 3D optical images, determining a thickness of the scanning target along the estimated trajectory of the x-ray for the predetermined pixel. In another example, determining the thickness of the scanning target further includes: registering a depth measurement from the 3D optical images with a global coordinate space to generate a 3D model of the scanning target in the global coordinate space; based on a geometry of the dual-energy x-ray source and the dual-energy x-ray detector, registering a trajectory of the emitted x-rays in the global coordinate space; and based on the trajectory of the emitted x-rays in the global coordinate space and the 3D model, determining a thickness of the scanning target for a predetermined pixel. In yet another example, determining the thickness of the scanning target further includes: modifying a template of a human body based on the captured 3D optical images; based on the modified template, identifying air gaps external to the human body caused by a shape of the human body; and adjusting the determined thickness based at least in part on the identified air gaps. In still another example, modifying the template includes registering template fiducial markers on the template with scanning target fiducial markers on the scanning target.

In another example of the above aspect, the method includes confirming a scanning target position based on the captured 3D optical images. In an example, confirming the scanning target position includes confirming the scanning target is located entirely within a scanning field. In another example confirming the target position includes confirming that body parts of the scanning target are not overlapping. In yet another example, the method includes determining, by a processor, based on the thickness of the scanning target and the dual-energy x-rays, an internal gaseous void in the scanning target. In still another example, the method includes performing a segmented bioimpedance analysis for at least one body part of the scanning target.

In another example of the above aspect, the method includes modifying the segmented bioimpedance analysis based on at least one of the detected the dual-energy x-rays. In an example, the method includes determining a total volume for the scanning target based on the captured 3D optical images. In another example, the method includes measuring a weight of the scanning target. In yet another example, the compartments include bone, fat tissue, and lean tissue. In still another example, the compartments include fat tissue, dehydrated lean tissue, and water.

In another example, the method includes based on the weight and the total volume of the scanning target, adjusting the value of at least one of the compartments. In yet another example, the patient is in a standing position and the method further includes rotating the scanning target on a rotating platform. In still yet another example, the method further includes generating 3D dual energy computed tomography images that are congruent with the captured 3D optical images. In another example, the emitted dual-energy x-rays are in the form of a fan beam, a pencil beam, or a cone beam. In yet another example, the method includes converting data based on the detected dual-energy x-rays to a two-material basis set and the two materials in the two-material basis set may be aluminum and acrylic.

In another aspect, the technology relates to a method for determining a composition of a scanning target, the method including: moving a dual-energy x-ray source and an x-ray detector along a scan path of the scanning target; emitting dual-energy x-rays; detecting the dual-energy x-rays after the dual-energy x-rays have passed through the scanning target; performing a segmented bioimpedance analysis for at least one discrete body part to determine an amount of water in the at least one discrete body part; and determining, by a processor, based on the dual-energy x-rays, a value of at least one compartment of bone, fat tissue, and lean tissue for the at least one discrete body part. In an example, the method includes determining a shape of a muscle tissue for the at least one discrete body part based on the detected dual-energy x-rays; and modifying the segmented bioimpedance analysis based on the determined muscle shape. In another example, the method includes, based on the determined shape of the muscle tissue, determining a position on the scanning target for attaching at least one electrode of a bioimpedance analysis device. In yet another example, the method includes, based on the determined shape of the muscle tissue, modifying a boundary line for processing of the dual-energy x-rays. In still another example, in the at least one discrete body part is at least one of an arm and a leg.

In another example of the above aspect, the at least one discrete body part is an arm, and a first electrode of a bioimpedance analysis device is attached to a shoulder associated with the arm and a second electrode of the bioimpedance analysis device is attached to a finger associated with the arm. In an example, the method includes capturing, substantially concurrently with the emission of the dual-energy x-rays, 3D optical images of the scanning target; determining a shape of the at least one discrete body part; and modifying the segmented bioimpedance analysis based on the determined shape of the at least one discrete body part. In another example, the method includes determining a muscle shape in the at least one discrete body part based on the detected dual-energy x-rays; and modifying the segmented bioimpedance analysis based on the determined muscle shape in the at least one discrete body part. In yet another example, the method includes capturing, substantially concurrently with the emission of the dual-energy x-rays, 3D optical images of the scanning target; determining a shape of the at least one discrete body part based on the captured 3D optical images; determining a muscle shape in the at least one discrete body part based on the detected dual-energy x-rays; and modifying the segmented bioimpedance analysis based on the determined shape of the at least one discrete body part and the determined muscle shape. In still another example, the bioimpedance data is captured from the scanning target subsequent to a scan of the scanning target.

This summary is provided to introduce a selection of concepts in a simplified form that are further described below in the Detailed Description. This summary is not intended to identify key features or essential features of the claimed subject matter, nor is it intended to be used to limit the scope of the claimed subject matter.

BRIEF DESCRIPTION OF THE DRAWINGS

The same number represents the same element or same type of element in all drawings.

Appendix A is an abstract regarding validation of methods and systems combining DXA technology and 3D optical technology.

Appendix B is an abstract regarding validation of methods and systems combining DXA technology and bioimpedance technology.

Appendix C depicts images related to a phantom being exposed to x-ray and optical imaging.

DETAILED DESCRIPTION

The present technology provides for a multiple modality scanning system and methods for determining body composition of a scanning target, such as a patient. By using multiple modalities as described herein, the results of the body composition analysis are improved and generally provide more accurate and detailed results describing the body composition of the patient. The scanning system may include a combination of two or more modalities, including: (1) dual-energy x-ray absorptiometry (DXA) technology, (2) three-dimensional (3D) optical scanning technology, and (3) bioelectrical impedance analysis (BIA) technology. In certain systems, all three modalities may be combined.

By including multiple modalities within the same scanning system, additional and often more accurate information about body composition may be obtained. For instance, the four-compartment (4C) model is often considered a useful model for human body composition. The model separates the body into bone mineral, adipose, water, and protein compartments, but traditionally requires several measurements including a total body water measurement using labeled water isotopes. The present multiple modality scanning system is able to resolve more compartments of the 4C model. For instance, as discussed above, DXA technology alone is unable to resolve more than two materials at any given pixel (e.g. bone and soft tissue). By combining the DXA technology with the 3D optical scanning technology, three or more compartments (e.g. bone, fat, and lean soft tissue) may be resolved using spatial information, such as thickness of a body portion, obtained from the 3D optical scanning technology. Such a results was previously unattainably from DXA technology. For instance, for a pixel for which bone was detected, traditional DXA systems could not resolve compositional differences in soft tissue that have been above or below the bone. The present technology is capable of resolving that soft tissue into two different compartments, such as lean tissue and fat tissue. By combining the DXA technology with the BIA technology, the compartments of the 4C model may also be resolved by incorporating the water measurements from the BIA technology with the results from the DXA technology. In addition, by incorporating all three modalities within the same scanning system, information from each of the modalities may be used to improve or validate the results from another modality without the requirements for separate procedures.

Figure 1A:
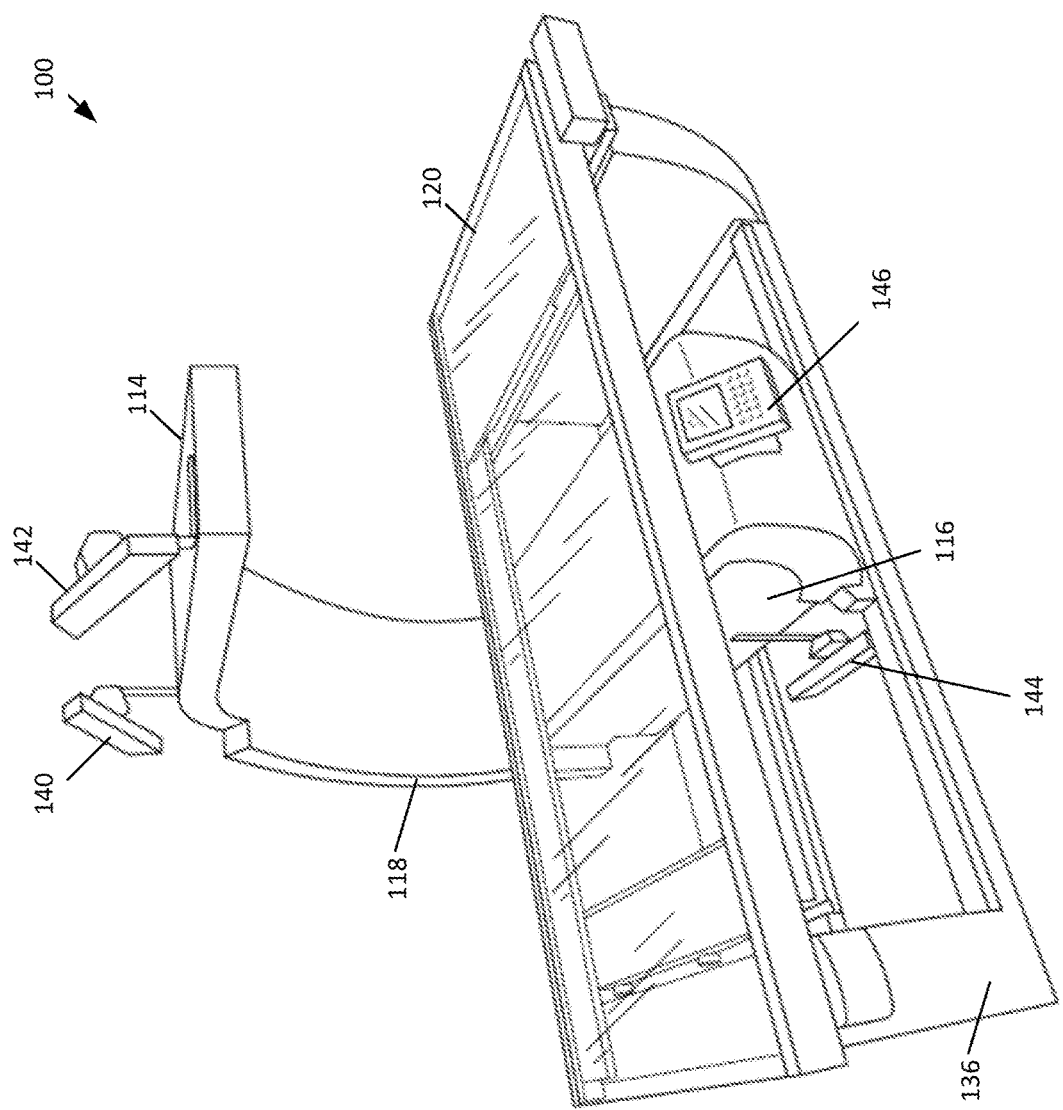
FIG. 1A depicts a perspective view of a multiple modality scanning system in accordance with one embodiment of the technology.
Figure 1B:
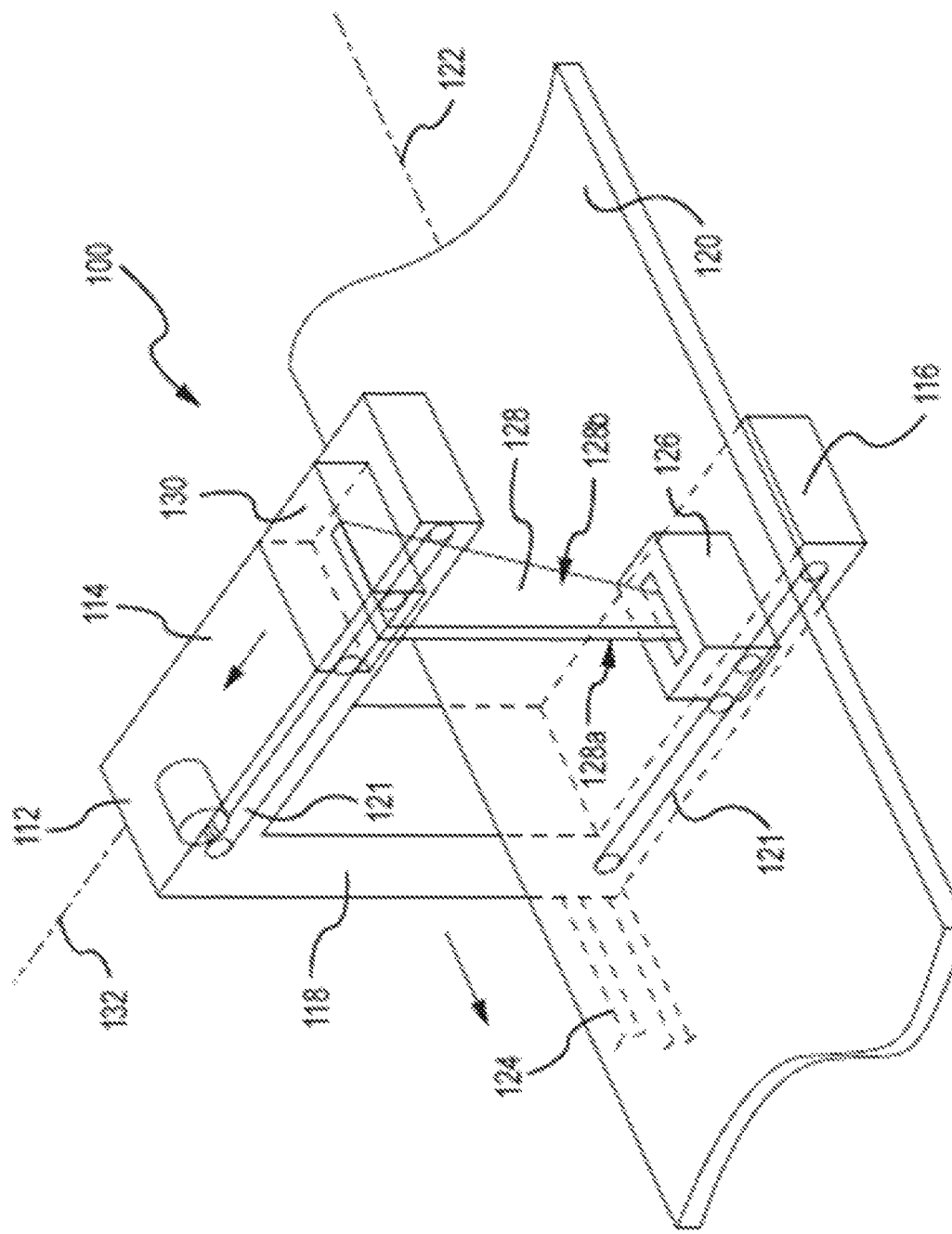
FIG. 1B depicts a perspective view showing internal components of a multiple modality scanning system in accordance with one embodiment of the technology.

FIG. 1A depicts a perspective view of a multiple modality scanning system 100 in accordance with one embodiment of the technology, and FIG. 1B depicts a perspective view showing internal components of a multiple modality scanning system 100 in accordance with one embodiment of the technology. FIGS. 1A-1B are discussed concurrently. The multiple modality scanning system 100 includes dual-energy x-ray absorptiometry components, 3D optical scanning components, and BIA components. The multiple modality scanning system 100 includes a support arm 112 having vertically opposed horizontal arms 114 and 116 separated by vertical bar 118. A horizontal planar patient support table 120 is disposed between the horizontal arms 114, 116 and extends along a longitudinal axis 122. A belt drive system 124 of a type well known in the art, allows motion of the support arm 112 longitudinally along longitudinal axis 122 for the length of the table 120. In other embodiments, other types of drive systems, including racks and gears, may be utilized. The longitudinal axis 122 of the table 120 is generally substantially parallel to a longitudinal axis of a patient lying on the table 120.

An x-ray source 126 is within the lower arm 116. The x-ray source 126 emits a collimated fan beam 128 of x-rays directed upward through the table 120. The beam 128 is detected or otherwise received by a linear detector 130. The fan beam 128 is oriented so that its narrowest extent 128a is along a transverse axis 132 and its widest extent 128b is along the longitudinal axis 122. As will be appreciated, the location of the x-ray source 126 and the detector 130 may be switched such that the x-ray source 126 is within the upper arm 114 and the detector 130 is within the lower arm 116.

The detector 130 includes a plurality of pixels that detect the x-rays emitted from the x-ray source 126.

The radiation source 126 emits dual-energy x-rays. The dual-energy x-ray source 126 may be a radioisotope or an x-ray tube running at constant voltage to produce a poly-energetic radiation beam. The beam may be subsequently filtered with a K-edge filter to form two energy modes. Alternatively, the radiation source 126 may be an x-ray tube run in a switched voltage mode where the voltage on the x-ray tube is periodically changed from a high to low voltage shifting the energy spectrum of the produced x-ray beam. For instance, low energy x-rays may be first produced, then the voltage of the source may be increased to produce higher energy x-rays. A brass filter may be used to filter the low energy x-rays when high energy x-rays are desired. Other techniques including rotating filter wheels and the like may be used to produce sequential dual energy beams. Data is acquired by a broad band detector 130 and detects high and low energy data that may be used in dual energy measurements. The detector 130 may also include detection elements for detecting high energy radiation and detection elements for detecting low energy radiation. In examples, where the radiation source 126 alternates or switches between high and low energy, the detector 130 may not need to separate high and low energy because the high and low energy emissions are separated in time. Where the high and low energy emission are not separated by time, the detector 130 separates the high and low energies during detection.

A plurality of 3D optical imaging devices 140, 142, 144 are also incorporated into the multiple modality scanning system 100. A first 3D optical imaging device 140 and a second 3D optical imaging device 142 are mounted to the upper arm 114. A third 3D optical imaging device 144 is mounted to the lower arm 116 on the opposite side of the table 120 from the first 3D optical imaging devices 140 and the second 3D optical imaging device 142. By arranging the 3D optical imaging devices 140, 142, 144 in such a manner, a 3D surface image may be obtained that captures all the visible surfaces of the patient 134, including the front, back, and sides of the patient 134. Each of the 3D optical imaging devices 140, 142, 144 may be any type of imaging device that is capable of capturing surface images suitable to create a 3D model of the surface of the patient 134. For example, each of the 3D optical imaging devices 140, 142, 144 may be a stereoscopic device, a laser scanning device, a structured light device, or a modulated light device, among others or a combination thereof. For instance, an imaging device may include two cameras and an infrared projector to generate structured light patterns. An example imaging device is the KINECT imaging device from the Microsoft Corporation of Redmond, Washington.

While three 3D optical imaging devices 140, 142, 144 are depicted in FIG. 1A, a greater or fewer number of 3D optical imaging devices may be incorporated depending on the particular type of imaging device and application. Similarly, while the 3D optical imaging devices 140, 142, 144 are depicted in particular locations and configurations in the figures, other configurations are also contemplated and possible depending on the particular type of imaging device and application. For example, two 3D optical imaging devices may be disposed below the table 120.

The table 120 is generally radiolucent so as to provide a support surface without significantly affecting the attenuation of the fan beam 128. In some examples, the table 120 is also optically translucent to allow for the 3D optical imaging camera 144 to image the side of the patient resting against the table 120. Each leg 136 of the table 120 may also include a scale or component for measuring the weight of the patient 134 lying on the table. For instance, by incorporating a scale into each of the legs 136, a more accurate weight of the patient 134 may be measured. Alternatively, a scale may be disposed remote from the table (e.g., elsewhere in an examination room). Data obtained from that scale may be directly communicated to the computing device described herein, or may be manually entered by a technician.

The x-ray source 126 and linear detector 130 may be moved transversely along the transverse axis 132. The x-ray source 126 and linear detector 130 are configured so as to move along the arms 114 and 116. This movement allows for transverse scans of the patient on the table 120. Motion of the x-ray source 126 and detector 130 is synchronized by belt-drive actuation mechanisms 121 as will be well understood to those of ordinary skill in the art. As with the belt drive system 124 described above, other types of drive mechanisms can be utilized in place of the belt-drive actuation mechanisms 124.

A bioimpedance machine 146 may also be incorporated into the multiple modality scanning system 100 and configured to perform bioimpedance spectroscopy analysis of a patient. The bioimpedance machine 146 may be mounted to the lower arm 116. In other examples, the bioimpedance machine 146 may be mounted to another component of the multiple modality scanning system 100. The bioimpedance machine 146 includes a set of electrodes or contacts that are connected to the patient 134. An electrical signal is sent through one or more of the electrodes and the signal is received through another one of the electrodes. As the electrical signal passes through the body, it is altered by different tissue of the body, and different frequencies of signals are altered differently as they pass through the body. For example, the electrical signal is less impeded by muscle tissue than it is by fatty tissue. Through the use of multiple frequencies, the intracellular water and extracellular water content may be determined, as will be appreciated by those having skill in the art.

A computing device including a display and other input/output options, such as those discussed below with reference to FIGS. 1E-1F, may be operatively coupled to the multiple modality scanning system 100 for displaying results or other information gathered or generated by the multiple modality scanning system 100, as discussed herein. For instance, the user interface may be operatively coupled through a network or wired connection to the multiple modality scanning system 100.

Figure 1C:
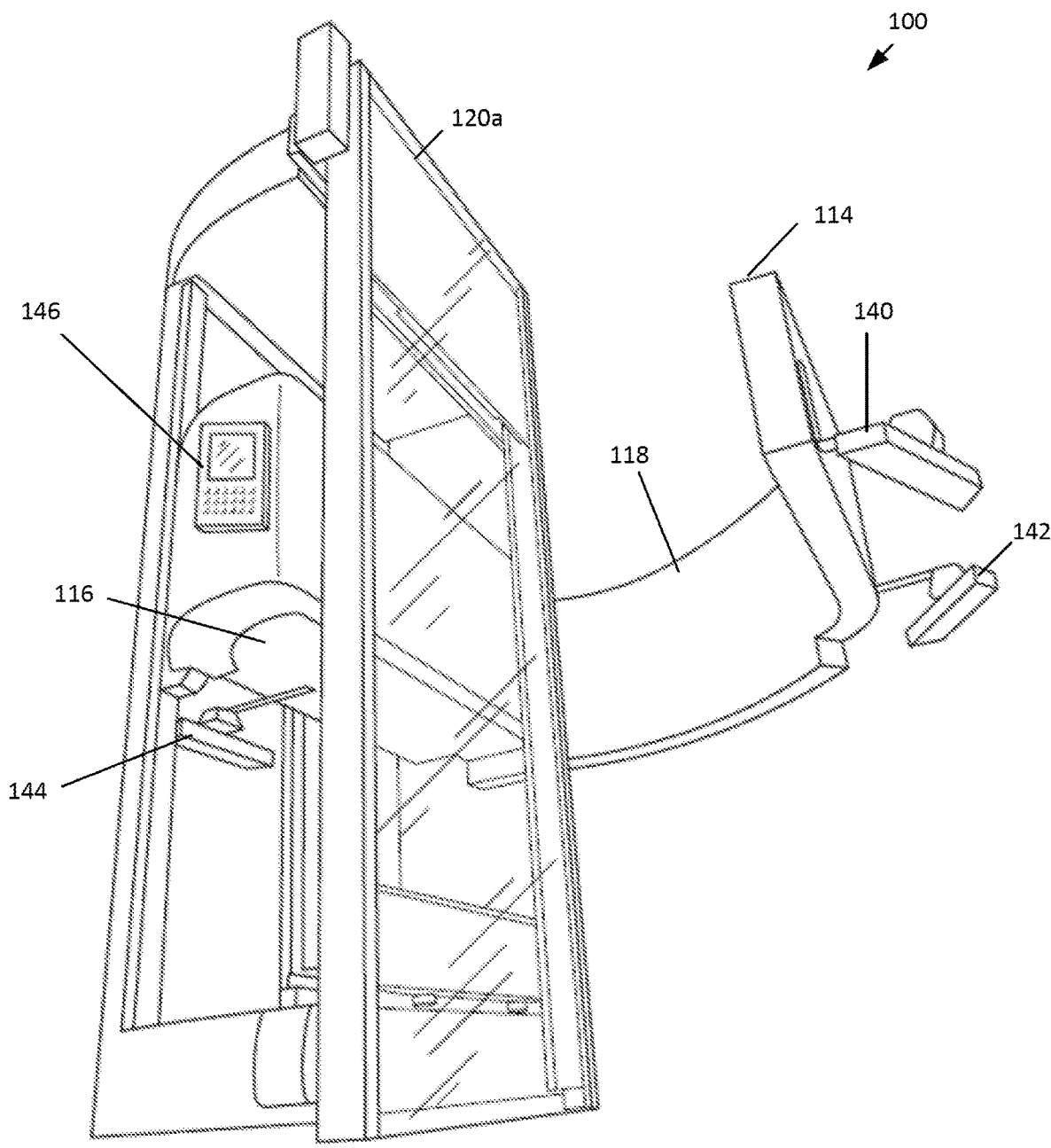
FIG. 1C depicts a perspective view of a multiple modality scanning system configured to scan a patient in the standing position in accordance with one embodiment of the technology.

FIG. 1C depicts a perspective view of a standing multiple modality scanning system 100 configured to scan a patient in the standing position in accordance with one embodiment of the technology. The standing multiple modality scanning system 100 is substantially similar to the multiple modality scanning system 100 depicted in FIG. 1A except the components have been rotated to accommodate scanning a patient in the standing position. As such, the shared components between standing multiple modality scanning system 100 and the multiple modality scanning system 100 have been labeled with the same reference numerals and share the function. The scale in the standing multiple modality scanning system 100, however, may be located underneath the standing position for the patient so as to accurately measure the weight of the patient. A rotating platform may also be included at the base of the standing multiple modality system. In such an example, the patient may rotate as optical and x-ray data is concurrently, or substantially concurrently, collected. As such, three-dimensional tomography images may be reconstructed from the dual energy x-ray data that are congruent with the 3D optical images of the same body locations.

Further, the standing multiple modality scanning system 100 may also include additional supports (not shown) for the patient to rest some of his/her weight to remain comfortable during the scan. In this example, the patient may lean against a radiolucent and transparent wall 120a so as to reduce fatigue during an examination. In further examples, the transparent wall 120a may not be included in the standing multiple modality scanning system 100, or the translucent wall 120a may also be a column or narrow support against which the patient may stand. Other supports, such as grips, armrests, or pads may also be incorporated to add comfort for the patient and help minimize patient movement during the scan. In some examples, grips, armrests, or pads may also be radiolucent and/or optically translucent.

Figure 1D:
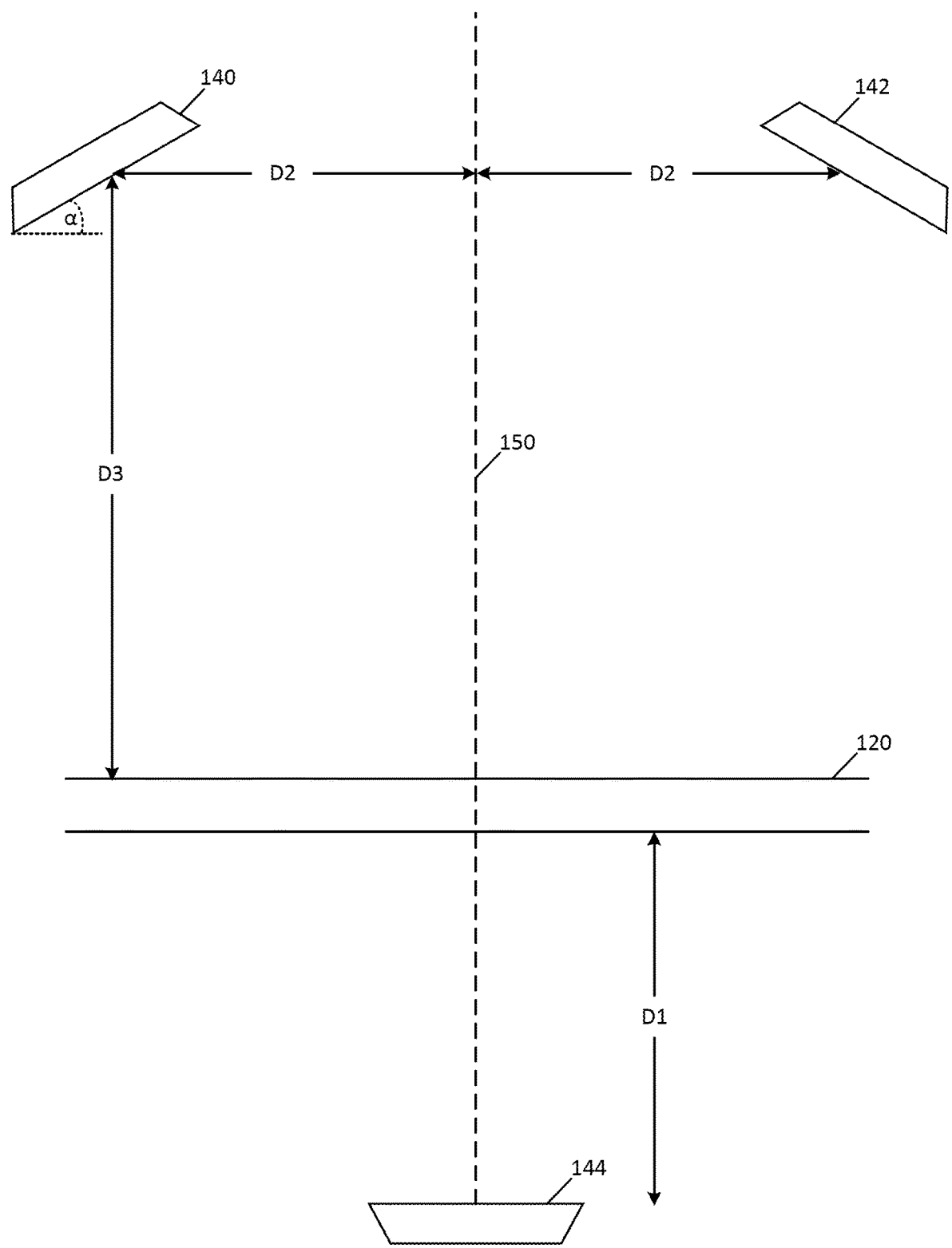
FIG. 1D depicts a schematic view of 3D optical imaging devices in a multiple modality scanning system in accordance with one embodiment of the technology.

FIG. 1D depicts a schematic view of 3D optical imaging devices 140, 142, 144 in a multiple modality scanning system 100 in accordance with one embodiment of the technology. The 3D optical imaging device 144 may be disposed on an opposite side of the table 120 (or wall 120a, not shown) from a patient. In this example, the 3D optical imaging device 144 is disposed so as to be centered with the table 120 such that it is aligned with a center line 150 of the table 120. The 3D optical imaging device 144 is positioned at a distance D1 from the table. In some examples, the distance D1 may be about 60 cm. In other examples, the distance D1 may be between about 40-80 cm.

The two 3D optical imaging devices 140, 142 located on an opposite side of the table 120, such that a patient is positioned between the two 3D optical imaging devices 140, 142 and the table 120. The two 3D optical imaging devices 140, 142 are spaced equidistantly from the center line 150 at a distance D2 therefrom. In an example, the distance D2 is about 26 cm. In other examples, the distance D2 may be from about 10-40 cm. The two 3D optical imaging devices 140, 142 may also be tilted to define an angle α between the imaging plane of each of 3D optical imaging devices 140, 142 and the plane of the table 120. In an example, the angle α is about 30 degrees. In other examples, the angle α may be from about 20-40 degrees. The two 3D optical imaging devices 140, 142 are located a distance D3 above the table 120. In an example, the distance D1 is about 84.5 cm. In other examples, the distance D1 may be about 60-100 cm. The distances D1, D2, D3 are measured to the center of the base of the respective 3D optical imaging device.

Figure 1E:
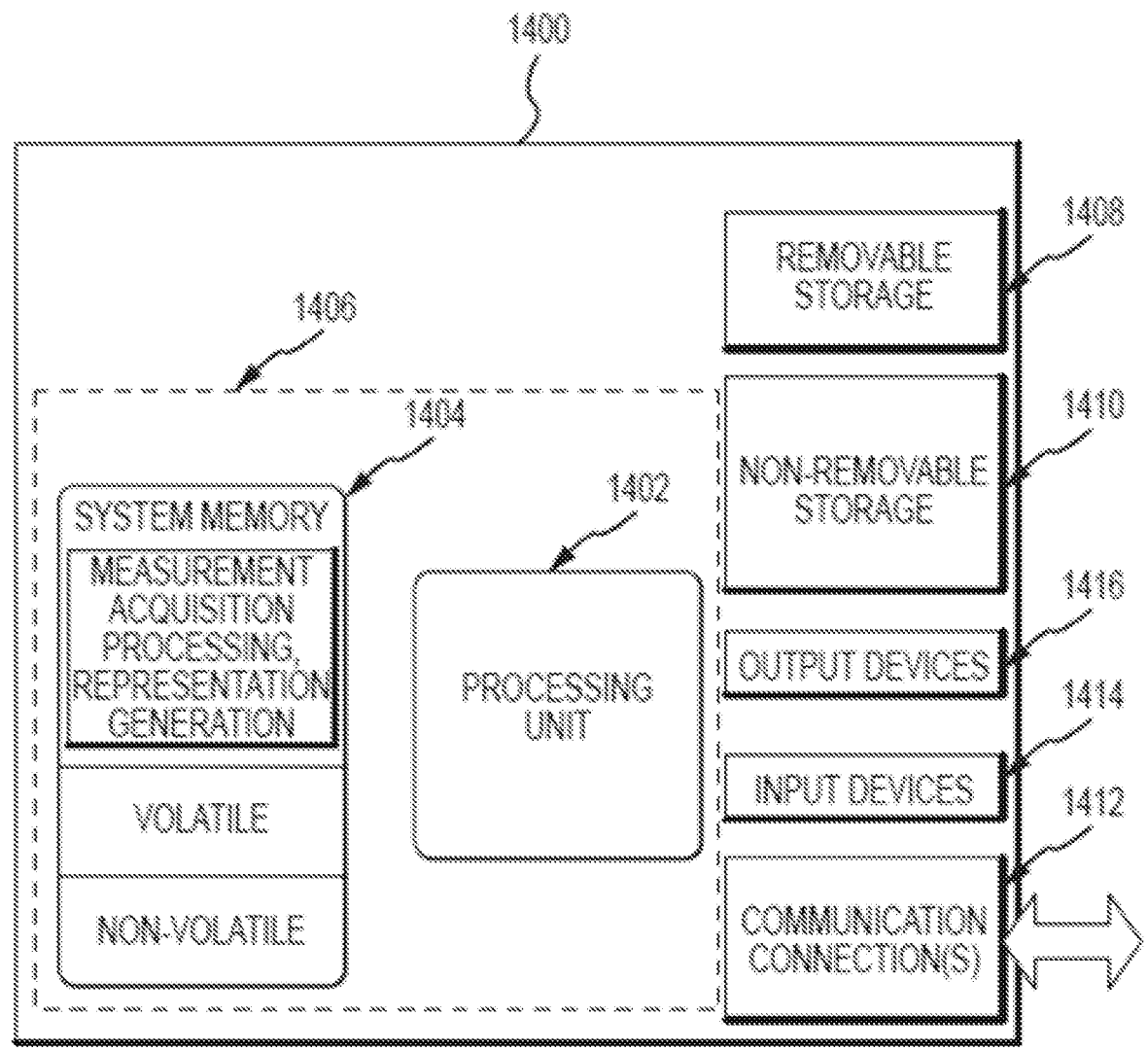
FIG. 1E depicts one example of a suitable operating environment in which one or more of the present examples can be implemented.

FIG. 1E depicts one example of a suitable computing device 1400 that may be coupled to the multiple modality scanning system 100. The computing device 1400 is a suitable operating environment in which one or more of the present examples can be implemented. This operating environment may be incorporated directly into the multiple modality scanning system 100, or may be incorporated into a computer system discrete from, but used to control, the multiple modality scanning system 100 described herein. This is only one example of a suitable operating environment and is not intended to suggest any limitation as to the scope of use or functionality. Other well-known computing systems, environments, and/or configurations that can be suitable for use include, but are not limited to, personal computers, server computers, hand-held or laptop devices, multiprocessor systems, microprocessor-based systems, programmable consumer electronics such as smart phones, network PCs, minicomputers, mainframe computers, tablets, distributed computing environments that include any of the above systems or devices, and the like.

In its most basic configuration, operating environment 1400 typically includes at least one processing unit 1402 and memory 1404. Depending on the exact configuration and type of computing device, memory 1404 (storing, among other things, instructions to perform the measurement acquisition, processing, and visual representation generation methods disclosed herein) can be volatile (such as RAM), non-volatile (such as ROM, flash memory, etc.), or some combination of the two. This most basic configuration is illustrated in FIG. 1E by dashed line 1406. Further, environment 1400 can also include storage devices (removable, 1408, and/or non-removable, 1410) including, but not limited to, solid-state devices, magnetic or optical disks, or tape. Similarly, environment 1400 can also have input device(s) 1414 such as touch screens, keyboard, mouse, pen, voice input, etc., and/or output device(s) 1416 such as a display, speakers, printer, etc. Also included in the environment can be one or more communication connections 1412, such as LAN, WAN, point to point, Bluetooth, RF, etc.

Operating environment 1400 typically includes at least some form of computer readable media. Computer readable media can be any available media that can be accessed by processing unit 1402 or other devices comprising the operating environment. By way of example, and not limitation, computer readable media can comprise computer storage media and communication media. Computer storage media includes volatile and nonvolatile, removable and non-removable media implemented in any method or technology for storage of information such as computer readable instructions, data structures, program modules or other data. Computer storage media includes, RAM, ROM, EEPROM, flash memory or other memory technology, CD-ROM, digital versatile disks (DVD) or other optical storage, magnetic cassettes, magnetic tape, magnetic disk storage or other magnetic storage devices, solid state storage, or any other tangible and non-transitory medium which can be used to store the desired information.

Communication media embodies computer readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer readable media.

The operating environment 1400 can be a single computer operating in a networked environment using logical connections to one or more remote computers. The remote computer can be a personal computer, a server, a router, a network PC, a peer device or other common network node, and typically includes many or all of the elements described above as well as others not so mentioned. The logical connections can include any method supported by available communications media. Such networking environments are commonplace in hospitals, offices, enterprise-wide computer networks, intranets and the Internet.

In some examples, the components described herein comprise such modules or instructions executable by computer system 1400 that can be stored on computer storage medium and other tangible mediums and transmitted in communication media. Computer storage media includes volatile and non-volatile, removable and non-removable media implemented in any method or technology for storage of information such as computer readable instructions, data structures, program modules, or other data. Combinations of any of the above should also be included within the scope of readable media. In some examples, computer system 1400 is part of a network that stores data in remote storage media for use by the computer system 1400.

Figure 1F:
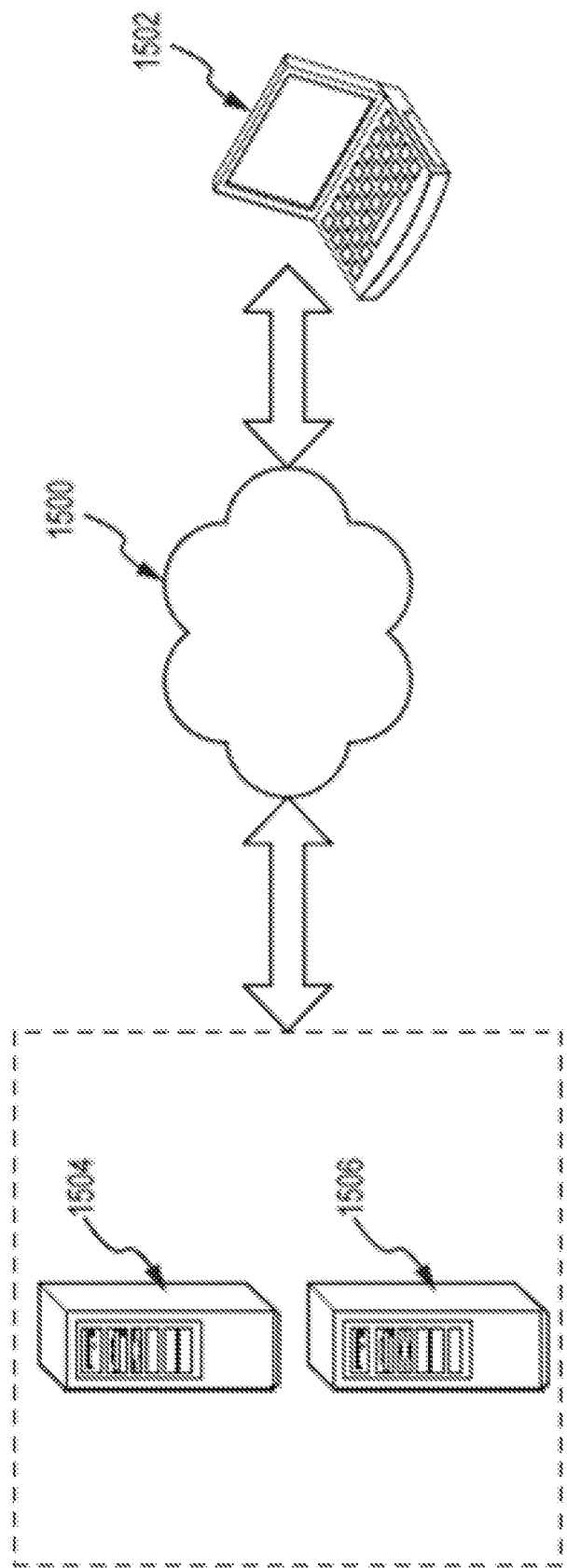
FIG. 1F depicts an example of a network in which the various systems and methods disclosed herein may operate.

FIG. 1F is an example of a network 1500 in which the various systems and methods disclosed herein may operate. In examples, a client device, such as client device 1502, may communicate with one or more servers, such as servers 1504 and 1506, via a network 1508. In examples, a client device may be a laptop, a personal computer, a smart phone, a PDA, a netbook, or any other type of computing device, such as the computing device in FIG. 1E. In examples, servers 1504 and 1506 may be any type of computing device, such as the computing device illustrated in FIG. 1E. Network 1508 may be any type of network capable of facilitating communications between the client device and one or more servers 1504 and 1506. Examples of such networks include, but are not limited to, LANs, WANs, cellular networks, and/or the Internet.

In examples, processing of data and performance of the methods described herein may be accomplished with the use of one or more server devices. For example, in one example, a single server, such as server 1504 may be employed to assist in processing data and performing the methods disclosed herein. Client device 1502 may interact with server 1504 via network 1508. In further examples, the client device 1502 may also perform functionality disclosed herein, such as scanning and processing data, which can then be provided to servers 1504 and/or 1506.

In alternate examples, the methods disclosed herein may be performed using a distributed computing network, or a cloud network. In such examples, the methods disclosed herein may be performed by two or more servers, such as servers 1504 and 1506. Although a particular network example is disclosed herein, one of skill in the art will appreciate that the systems and methods disclosed herein may be performed using other types of networks and/or network configurations. Further, the data sent to the servers and received from the servers may be encrypted. The data may also be stored in an encrypted manner both locally and on the servers.

Figure 2:
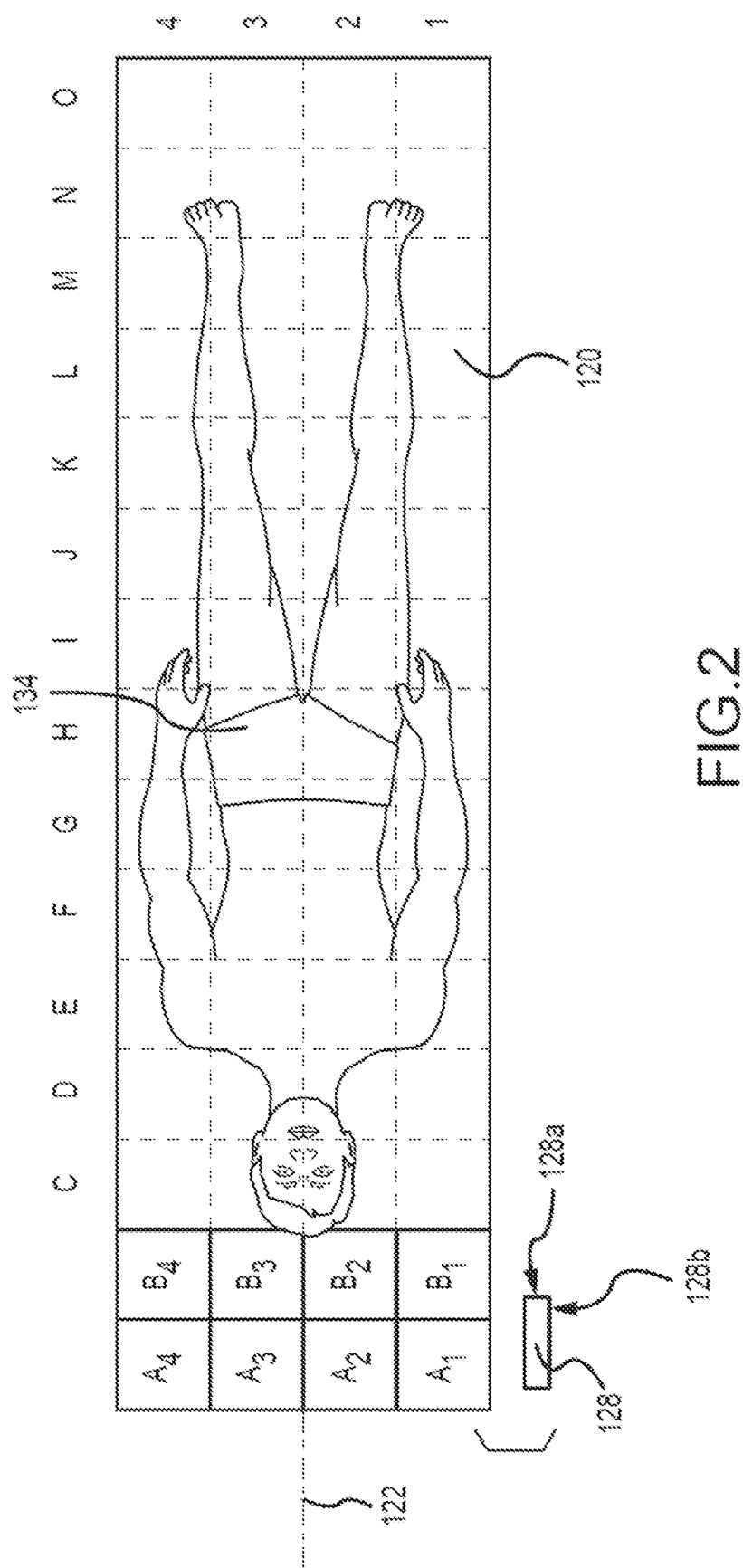
FIG. 2 depicts a top plan view of the table of the multiple modality scanning system of FIGS. 1A-1B.

FIG. 2 depicts a plan view of the table 120 of the multiple modality scanning systems 100 of FIGS. 1A-1D. Certain of the components described above are not depicted in FIG. 2 for clarity. The fan beam 128 may be scanned over the surface of table 120 and hence may scan the whole body of patient 134 so as to generate a series of transversely extending scan images that may be merged into a single composite image or data set. Alternatively, a plurality of scan images can be merged into a single composite image for a particular body structure or part. For example, a first scan image may encompass, in sequence, areas A1, A2, A3, and A4. The x-ray source and linear detector, described above, may move transversely as required, emitting and receiving x-ray energy along the various sequential areas. At the end of this scan, motion of the support arm, described above, in the longitudinal direction may be performed. For example, the support arm may move towards the feet of the patient, so as to align with a second area of the patient such that the detector may perform a second scan image. The second scan image may be in order of areas B4, B3, B2, and B1. Alternatively, the arm may return to the side of the table 120 where it began the first image scan and scan areas B1, B2, B3, and B4. Because the transverse width of the patient 134 is substantially less than the superior to inferior height of the patient, each scan image, e.g., all of areas 1-4 in each of path A or path B, is acquired at a time closely proximate to its adjacent scan images and thus the risk of patient motion and the amount of patient motion may be substantially reduced. This is one of several marked advantages over imaging systems that that perform scans along the longitudinal axis of the patient. As should be appreciated, other types of x-ray sources and scanning techniques may be implemented to conduct a DXA scan of the patient 134. For instance, pencil beam or a cone beam may be utilized. Scanning techniques, such as using a single pass of the patient for the scan, conducting multiple scans, utilizing raster scan techniques, or other similar scanning techniques are all possible.

Three-dimensional optical images are also captured substantially concurrently with the emission of x-rays during the scan. For instance, when x-rays are emitted from the x-ray source, 3D optical images are captured from the 3D optical imaging devices at substantially the same time. The optical images may be captured just before, simultaneously with, or just after the emission of the x-rays and be considered to be captured substantially concurrently with the emission of x-rays. In some examples, the optical images are captured within one second before or after the emission of x-rays. The 3D optical images also capture images of at least the same body portion for which the emitted x-rays are passing through. By capturing the 3D optical images substantially concurrently with the emission of x-rays, the captured 3D optical image will capture the position and shape of the patient at approximately the same time as the dual-energy x-ray information is obtained. Thus, data extracted from the 3D optical images, such as body portion thickness, may be accurately correlated with the data from the dual-energy x-rays. The 3D optical devices that obtain the optical images may be configured to move similarly to the x-ray source and detector. That is, the 3D optical devices and x-ray source may move and image areas A1, A2, A3, and A4. Alternatively, the 3D optical devices may be fixed so as to prevent movement thereof transverse to the axis 122. In such a case, while the x-ray source images areas A1, A2, A3, and A4 sequentially, the 3D optical devices may image areas A1-A4 simultaneously. The x-ray source may then sequentially image areas B4, B3, B2, and B1, while the 3D optical devices image areas B1-B4 simultaneously. Other scanning paths are contemplated. As should be appreciated, while the patient 134 is depicted as lying on the table 120, similar scanning techniques may be performed for a patient in a standing position using the standing multiple modality system 100. For instance, three-dimensional optical images are also captured substantially concurrently with the emission of x-rays during the scan such that the optical images can be correlated with the measurement of the x-rays.

In other embodiments, transverse scans of particular or discrete body parts may be performed. In one example, a complete transverse scan of the ribcage may include scans along scan paths E, F, G, and H. A transverse scan of a single body part that does not extend across an entire transverse scan path can also be performed. For example, the left femur may be scanned by imaging areas I1, I2, J2, J1, K1, and K2. Other transverse scan paths are contemplated.

Figure 3:
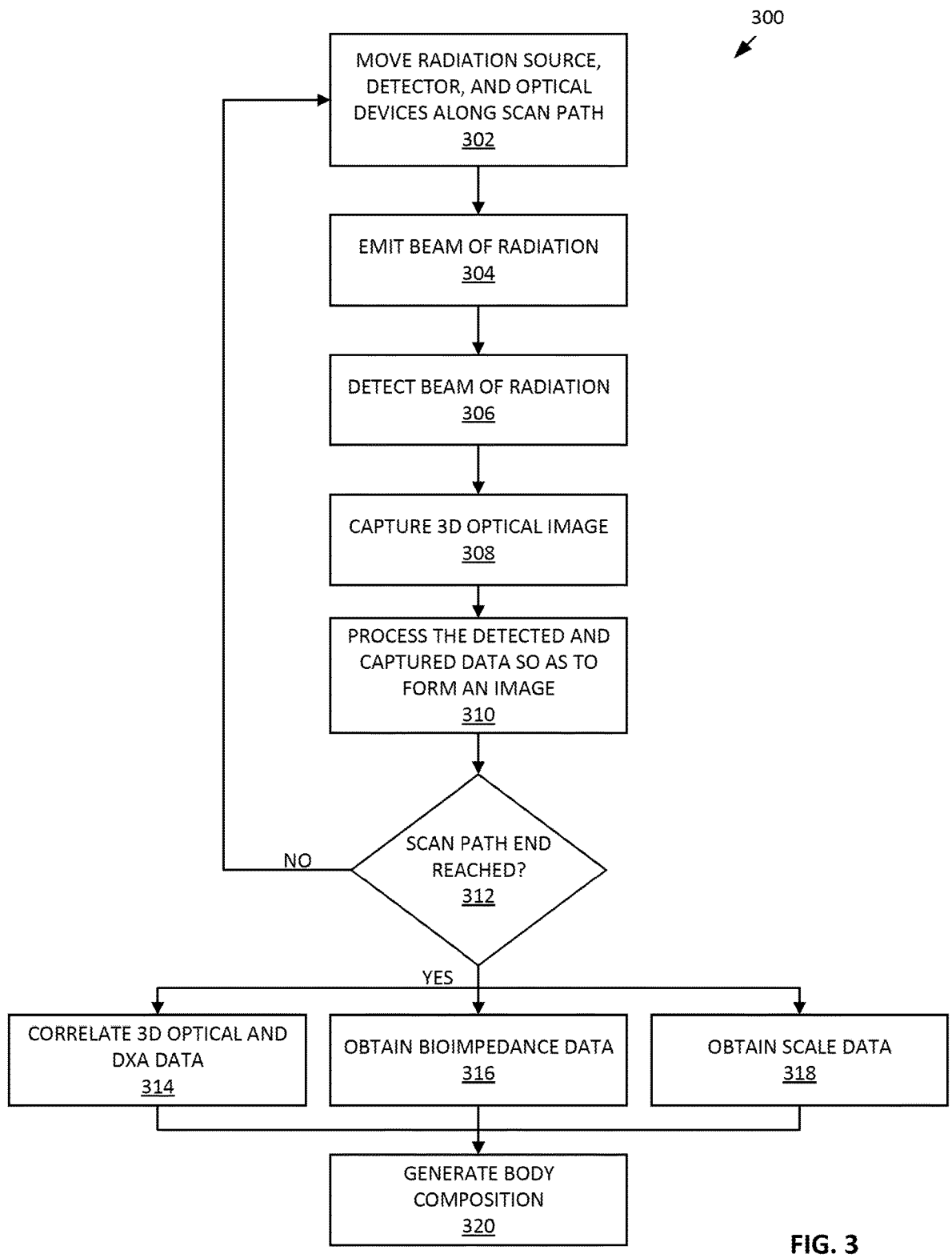
FIG. 3 depicts a method of generating body composition data from a scanning procedure in accordance with an embodiment of the technology.

FIG. 3 depicts a method 300 of generating body composition data from a scanning procedure in accordance with an embodiment of the technology. The method 300 provides for a multiple modality scanning system having a radiation source collimated to produce or emit a beam of radiation directed across a patient to an electronic radiation detector, the latter of which receives, detects, or otherwise measures the beam of radiation passing through the patient. A scanning assembly moves the radiation source and radiation detector along at least one scan path transverse to a longitudinal axis of a patient at operation 302. While moving, the radiation source emits the beam of radiation, operation 304, which is detected by the radiation detector at operation 306. Substantially concurrently with the emission and detection of the radiation, 3D optical data, such as images, are captured by one or more 3D optical imaging devices at operation 308. By capturing the optical images substantially concurrently with the emission of radiation, the optical images more accurately capture the patient's configuration and position at the same time a particular portion of the patient is being scanned with the dual-energy x-rays.

The detected beam and/or the captured optical data may then be processed so as to form an image, or a portion thereof, at operation 310. For instance, a 3D model of the patient may be generated from the 3D optical data. In addition, because the beam has a predefined width, the size of each image may be based on the beam width and a length of travel of the scanning assembly. Any number of discrete images may be formed as the scanning assembly travels along the transverse scan path. As the scanning assembly traverses the scan path, one or more sensors determine a position thereof. In operation 310, the composite image may then be stored, displayed, and/or otherwise utilized for marking and analysis of tissue, as described herein. If the end of the scan path is not reached as depicted in operation 312, flow branches to NO and movement of the scanning assembly (as well as operations 302-310) continue, thus generating a plurality of images along the scan path. Once the end of the scan path is reached at operation 312, flow branches YES, where additional information may be obtained and further processing occurs.

The patient support table may support a supine patient with the patient's head and feet lying along a longitudinal axis and the scanning assembly may move the radiation source and electronic detector along a series of transverse scan paths substantially perpendicular to the longitudinal axis across the patient to acquire the scan images. Such a method includes operations similar those depicted in FIG. 3. As the end of a scan path is reached, the system may then traverse a second transverse scan path that is substantially parallel to the first transverse scan path.

Once the scanning has been completed, or during the scanning in some examples, the captured 3D optical data is correlated with the DXA data at operation 314. As an example, correlating the 3D optical data and the DXA data may include determining the thickness of the patient on a pixel-by-pixel basis. For instance, a ray-tracing method may be used to determine a thickness of a patient corresponding to a particular pixel of the detector. Determining the thickness of the patient on a pixel-by-pixel basis is discussed further with regard to FIGS. 4-6, below.

The DXA data may also be transformed into a two material basis set. For instance, the DXA data may be converted to thicknesses of two appropriate basis materials, such as aluminum and acrylic thickness or water and fat thickness. A discussion of basis sets and techniques that may suitable here are set forth in Lehmann L A, Alvarez R E, Macovski A, Brody W R. Pelc N J. Riederer S J and Hall A L 1981 *Generalized image combinations in dual kVp digital radiography* Med. Phys. 8 659-67, DOI 10.1118/1.595025, which is incorporated herein by reference in its entirety. In the present technology, an equivalent areal density ($g/cm^2$) of each of the two materials may be measured with a DXA system. That measurement may then be combined with the 3D optical data. The optical data may also represented in units of areal density ($g/cm^2$) based on an assumption that the density of the patient has a similar density as water (1 $g/cm^3$) or by using a measured or average density of the patient based on the patient's weight and volume determined from the optical data. An example of the technique described by Lehmann is shown in Appendix C. FIG. A is an image of an entire Whole Body phantom (available from Hologic, Inc., of Marlborough, Massachusetts) as either the thickness of Aluminum, or the thickness of Acrylic (aka Lucite). Each pixel has been expressed as having a certain thickness in mm of Aluminum and a certain thickness in mm of Acrylic. FIG. B is a 2D histogram, with each circle representing a single pixel in FIG. A. FIG. C depicts the spine area of the phantom, and FIG. D is a 2D histogram of the spine area. It can be appreciated that the aluminum spine of the phantom has a greater thickness of aluminum per pixel in both the image and the 2D histogram, than the part of the image that does not contain the aluminum spine. What is also apparent is that the total thickness of the plastic not containing the spine is approximately 130-135 mm of Lucite, as measured by the dual-energy x-ray data. The actual thickness of the spine phantom is greater than 135 mm, which can be determined by the optical data. This indicates that the plastic of the spine phantom is not acrylic—in fact it is low density polyethylene. Data on the thickness of the phantom thus adds information that could not be obtained using only the dual-energy x-ray data.

Bioimpedance analysis data may also be obtained at operation 316. The bioimpedance data is obtained through a bioimpedance machine by attaching electrodes to the patient. The bioimpedance analysis is performed in a segmented manner wherein portions, or segments, of the body are specifically analyzed with the bioimpedance machine. For example, where information is desired for an arm of a patient, one electrodes of the bioimpedance machine may be attached to the patient's shoulder and another electrodes may be attached to the patient's finger. The positioning of the electrodes may also be modified based on the obtained optical data and/or the DXA data, as discussed further below with respect to FIG. 8. The bioimpedance analysis data may be obtained during the scanning of the patient or after the scanning of the patient. In some examples, more accurate results may be obtained by performing the bioimpedance analysis following the scan due the patient having remained substantially still for the duration of the scanning process.

The weight of the patient may be also be obtained in operation 318 by measuring the patient's weight with a scale. For instance, weight data may be received from a scale component incorporated into each of the legs of a patient support table in a multiple modality scanning system.

Based on the data obtained, including the DXA scan data, the 3D optical data, the bioimpedance data, and the weight data, the body composition of the patient is generated using some or all of the data obtained in operation 320. In some examples, the body composition may be generated on a pixel-by-pixel level and/or on a body portion or segment basis. In determining body composition on a pixel-by-pixel level, three types of tissue may be resolved for each pixel using the thickness of the patient for the particular pixel determined in operation 314. For pixels that include bone, the body composition includes determining amounts of bone, lean tissue, and fat tissue. For pixels that do not include bone, the generating body composition includes determining amounts of fat tissue, dehydrated lean tissue, and water. Accordingly, when the body composition for each of the pixels are combined to determine a body composition for a portion of the body, such as an arm, four compartments are generated including bone, dehydrated lean tissue, fat tissue, and water. The amounts or values of the compartments may be represented as percentages, areal densities, masses, volumes, or any other values known by those having skill in the art for representing the body composition compartments. One example for determining the three compartments for body composition on a pixel-by-pixel basis using the thickness of the patient and DXA data is set forth in Malkov S, Shepherd J. Combining 3D optical imaging and dual energy absorptiometry to measure three compositional components. *Proceedings of SPIE-the International Society fir Optical Engineering.* 2014; 8937:893714-. doi:10.1117/12.2040903, which is incorporated herein by reference in its entirety.

The bioimpedance analysis data along with the DXA data may also be used to generate body composition for a particular body portion or segment. For example, by receiving segmented bioimpedance analysis data for an arm of a patient, an amount of water may be ascertained for the arm of the patient. The amount of water determined through the BIA data may be combined with the DXA data to provide the compartments of the 4C model. A method for combining DXA data and BIA data for a whole body analysis is set forth in Wilson J P, Strauss B J, Fan B, Duewer F W, Shepherd J A. Improved 4-compartment body-composition model for a clinically accessible measure of total body protein. *Am J Clin Nutr.* 2013; 97:497-504. doi: 10.3945/ajcn.112.048074. PubMed PMID: 23364008, which is incorporated herein by reference in its entirety. While the preceding reference discusses whole body BIA data, the reference does not address the use of segmented BIA data, such as BIA data for a discrete body part. The combination of segmented BIA data and DXA data is often not a straightforward operation. For instance, determining proper electrode location to measure a discrete body part that accurately aligns with the DXA data is a challenging task. Solutions to this problem are discussed in further detail below with respect to FIG. 8.

The weight of the patient may also be utilized in generating the body composition. In some examples, the weight of the patient may be used as a verification of the body composition determined from the DXA data along with the 3D optical data and/or the bioimpedance data. For instance, based on the determined body composition from the DXA data and the 3D optical data, an overall volume for the patient can be determined. Due to the known densities of the different compartments, a mass for the patient may also then be calculated. That mass can be compared to the measured weight of the patient to verify the generated body composition data. The weight may also be used to modify the generated body composition data where the estimated mass or weight of the patient differs from the measured mass or weight of the patient.

The body composition data generated from the DXA data and the 3D optical data may also be compared against the body composition data generated from the DXA data and the bioimpedance data. If the results differ by more than a predetermined threshold, then an error message may be displayed indicating a potentially inaccurate scan. In some embodiments, the body composition results from the DXA data and the 3D optical data may be merged with the body composition data generated from the DXA data and the bioimpedance data. For instance, the two sets of body composition data may be averaged or modified by a predetermined factor or set of weights to compensate for differences between the two data sets.

Figure 4:
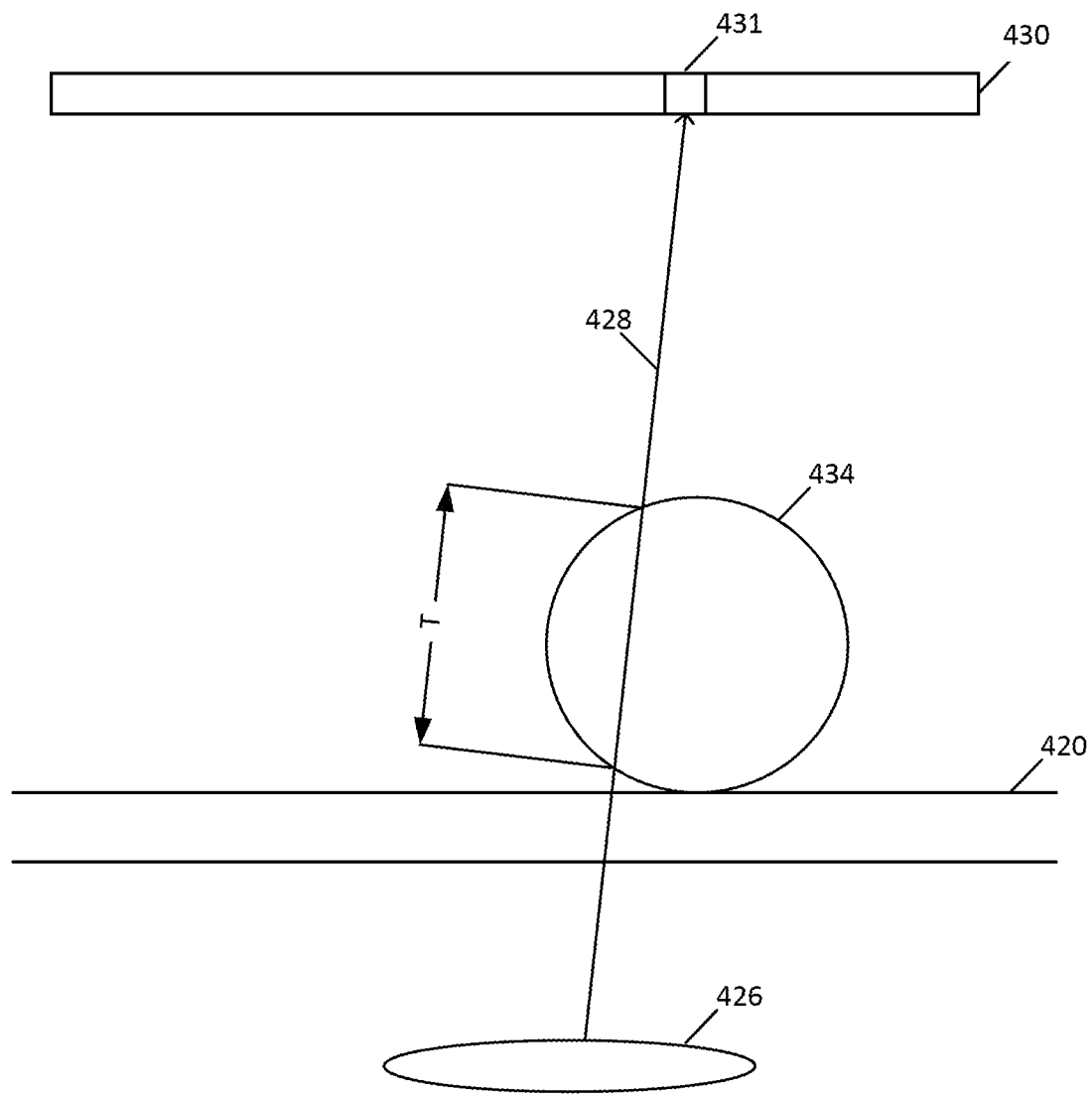
FIG. 4 depicts a schematic cross-section view of the scanning technology to determine thickness of the scanning target in accordance with an embodiment of the technology.

As discussed above, the captured 3D optical data may be used to determine the thickness of the patient on a pixel-by-pixel level. To determine that thickness, a ray tracing algorithm may be implemented to determine the thickness of a particular ray, or subset of rays, emitted from the x-ray source and reaching the particular pixel. FIG. 4 depicts a schematic cross-section view of the multiple modality scanning system 400 to determine a thickness T of a scanning target, such as a patient 434, in accordance with an embodiment of the technology. The multiple modality scanning system 400 may be the same as the multiple modality scanning systems 100 depicted in FIGS. 1A-1F above. Multiple modality scanning system 400 includes an x-ray source 426 that emits dual-energy x-rays towards a patient 434 on a table 420. The x-rays are detected by a detector 430 after passing through the patient 434. One ray 428 emitted from the x-ray source 426 is depicted in FIG. 4. The ray 428 is emitted from the x-ray source 426, passes through a portion, such as a leg or other appendage, of the patient 434, where it is detected by a pixel 431 of the detector 430. Accordingly, the thickness T of the patient 434 corresponding to the particular ray 428 is the distance the ray 428 travels through the patient 434. That thickness T may then be used, in combination with the DXA data for the pixel 431, to generate body composition data for the pixel 431. As should be appreciated, while the ray 428 is depicted as a single ray, it may be a collection of rays that are detected by the particular pixel 431. Further, the ray 428 may be representative of central ray of the collection of rays that are detected by the particular pixel 431.

Figure 5:
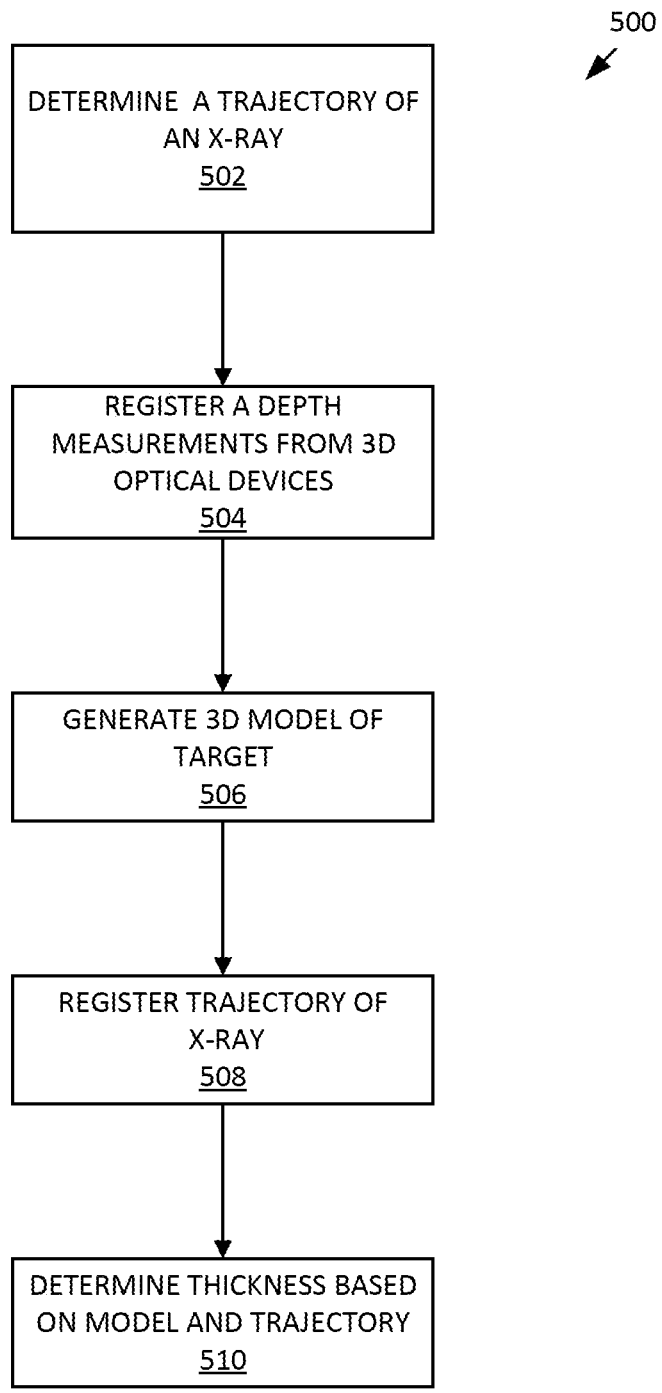
FIG. 5 depicts a method of determining the thickness of the scanning target in accordance with an embodiment of the technology.

FIG. 5 depicts a method 500 of determining the thickness of the scanning target, such as a patient, in accordance with an embodiment of the technology. Determining the thickness T described above in FIG. 4 requires overcoming substantial obstacles caused by the geometries of two different imaging systems, e.g., the DXA imaging technology and the 3D optical imaging technology. The x-ray source and the linear detector generally fit well to one set of coordinates, while the 3D optical devices generally fit well to separate sets of coordinates. In general, these multiple sets of coordinates do not immediately lend themselves to simple calculations or determinations. The method 500 provides a solution to determining the thickness of a patient corresponding to a particular pixel despite having multiple imaging systems with different geometries.

At operation 502, a trajectory of an x-ray corresponding to a particular pixel may be determined. The trajectory may be an estimated trajectory based on the location and geometry of the x-ray source and the particular pixel for which a patient thickness is desired. At operation 504, depth measurements from one or more 3D optical devices may be registered to a global coordinate space. The global coordinate space may be grounded, or have an origin, based on one of the components within the multiple modality scanning system, such as the table. In such an example, the origin of the global coordinate system may be the center of the table. In other examples, the origin of the global coordinate system may be a portion of the moving support arm, the x-ray source, the linear detector, or one of the 3D optical devices. In some examples, in operation 504, the depth measurements from the 3D optical devices may only be registered for a body part for which the ray passes through based on the estimated trajectory. Based on the registered depth measurements from the 3D optical devices, a 3D model for the patient, or a body part of the patient, is generated in the global coordinate space at operation 506. The 3D model of the patient depicts the patient in three-dimensions such that a depth can be determined in the global coordinate space.

At operation 508, the trajectory of the x-ray corresponding to the desired pixel is registered to the global coordinate space. Registering the x-ray to the global coordinate space involves accounting for the geometries and locations of the x-ray source and the detector as compared to the geometries and locations of each of the 3D optical devices. At operation 510, once the trajectory of the x-ray is registered to the global coordinate space, the thickness of the patient corresponding to a particular pixel is determined from the 3D model of the patient in the global coordinate space. That thickness may then be used to generate body composition data corresponding to the particular pixel, as discussed above. The method 500 may be a part of operation 314 in method 300 depicted in FIG. 3.

Figure 6:
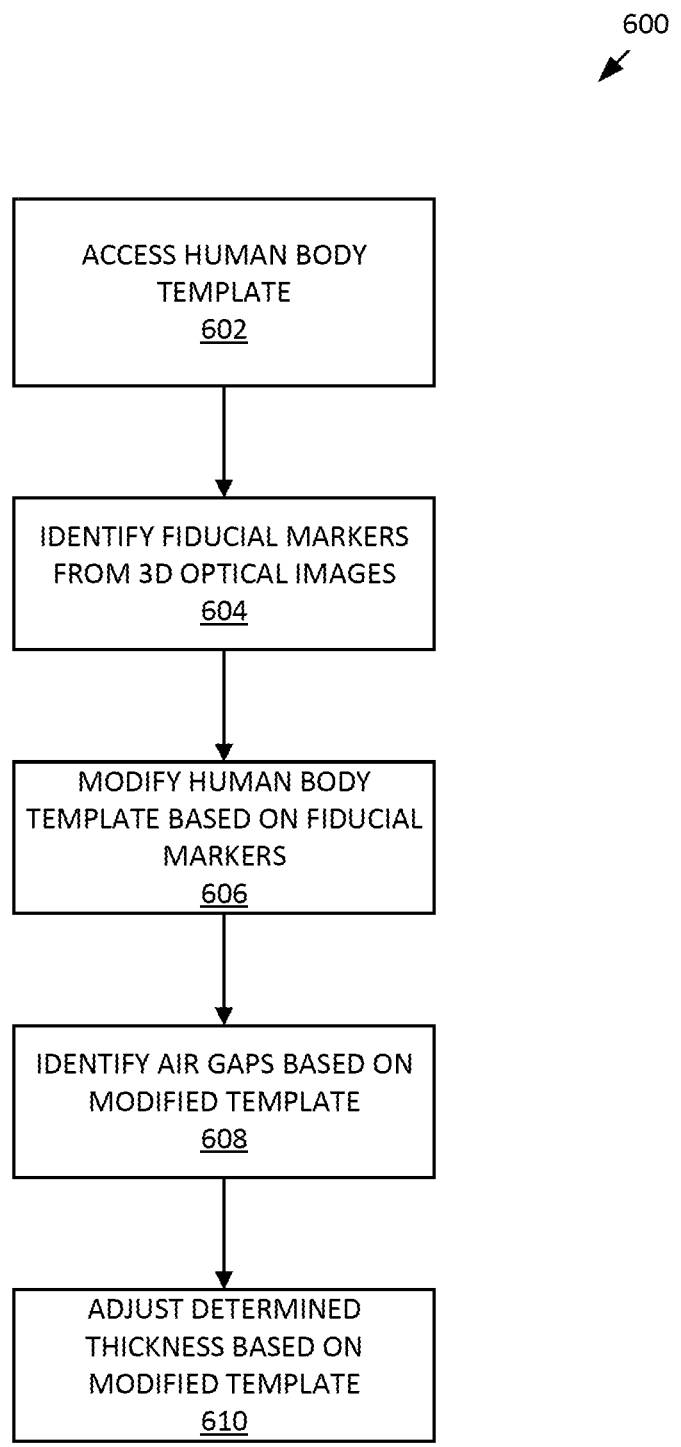
FIG. 6 depicts a method for modifying a determined thickness of the scanning target in accordance with an embodiment of the technology.

The thickness determined from the 3D optical data, such as thickness determined in method 500, however, may contain inaccuracies due to the 3D optical data being limited to surface scans of the patient. For example, air gaps may exist in between external surfaces of the patient, such as the hollow area in the underarm beneath the junction of the arm and the shoulder. If a thickness is determined for an x-ray that passes through the underarm based on a 3D model from surface imaging, the thickness may be incorrect because the air gap may not be captured by the 3D model. FIG. 6 depicts a method 600 for modifying a determined thickness of the scanning target in accordance with an embodiment of the technology. The method 600 utilizes a template of a typical human and modifies the template to be more similar to the actual patient being scanned. Air gaps in the patient are then estimated based on the modified template and used to adjust the thickness of the patient.

More specifically, at operation 602 in method 600, a standard template of a human body is accessed. Fiducial markers or other landmarks of the patient are identified from the 3D optical images at operation 604. The fiducial markers or landmarks of the patient may be identified from a 3D model of the patient generated from the captured image data from the 3D optical devices. One or more of the fiducial markers or other landmarks identified on the patient are then correlated to the human body template. At operation 606, the human body template is then modified to match the fiducial markers or landmarks identified on the patient. Air gaps in the modified template are then identified at operation 608. For instance, an air gap in the underarm or the intergluteal cleft of the modified template may be identified. At operation 610, a thickness determined for the patient for a particular pixel, such as the thickness determined in method 500 depicted in FIG. 5, is adjusted based on the identified air gap if the x-ray reaching the particular pixel passed through the air gap. For example, to determine if the x-ray passed through the air gap, the modified template may be aligned with the 3D model of the patient generated from the captured 3D images of the patient. Once the 3D model and the modified template are aligned, a determination can be made if the x-ray passed through any of the air gaps identified in the modified template. If the x-ray did pass through an identified air gap, the thickness of the patient for the particular pixel is reduced based on the size and shape of the identified air gap. The adjusted thickness may then be used in generating body composition data, such as in operation 320 of method 300 depicted in FIG. 3.

Figure 7:
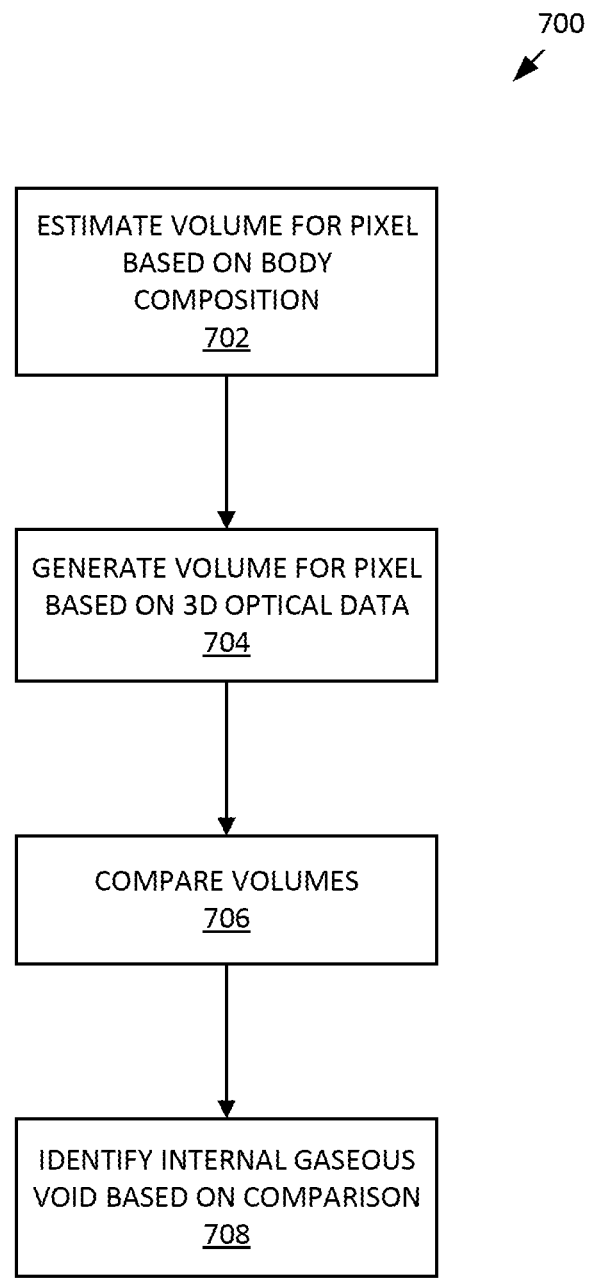
FIG. 7 depicts a method for identifying internal gaseous voids within a scanning target in accordance with an embodiment of the technology.

While method 600 identifies air gaps between exterior surfaces of the patient, such as in the underarm, the present technology may also be used to identify internal gaseous voids within a patient. FIG. 7 depicts a method 700 for identifying subcutaneous gaseous voids within a scanning target in accordance with an embodiment of the technology. At operation 702, a volume for a portion of the patient can be determined for one or more pixels based on the body composition data generated in method 300 depicted in FIG. 3. One method for determining volume from DXA data and/or body composition data is set forth in Wilson J P, Mulligan K, Fan B, et al. Dual-energy X-ray absorptiometry—based body volume measurement for 4-compartment body composition. *The American Journal of Clinical Nutrition.* 2012; 95(1):25-31. doi:10.3945/ajcn.111.019273, which is incorporates herein by reference in its entirety. A volume for a particular pixel or set of pixels is generated based on the 3D optical data in operation 704. The volume may be determined from the 3D optical data by using the shape and size of each pixel and the thickness determinations discussed above. For example, the volume of the patient corresponding to one or more pixels may be generated from a 3D model of the patient generated from the captured 3D image data. The volume determined from the body composition data and/or DXA data is compared to the volume generated from the 3D optical data at operation 706.

In operation 708, the internal gaseous voids within the patient are identified based on the comparison of volumes in operation 706. If the volume determined from the 3D optical data is greater than the volume predicted from the body composition data, there may be an abnormal gaseous void inside the patient at a location along the trajectory or the x-ray(s) corresponding to the one or more pixels for which the volume was determined. In some instances, internal gaseous voids are to be expected, such as in the lungs. In the abdomen, however, such gaseous voids may be abnormal and may be indicators of potentially serious conditions. Accordingly, a modified human body template, such as the modified human body template generated in operation 606 in method 600 depicted in FIG. 6 may be used a baseline for comparison. For instance, the modified human body template may indicate a location or volume of the lungs or other expected gaseous voids within a standard human body. If the difference between the compared volumes in operation 706 exceeds a predetermined threshold, an abnormal gaseous void may be predicted. For instance, if the difference between the compared volumes in operation 706 is greater than the volume difference predicted from the modified human template, an abnormal gaseous void may be predicted. Similarly, if there is a difference between the compared volumes in operation 706 for an area where gaseous voids are unexpected, an abnormal gaseous void may be predicted to exist in the patient. Certain gaseous voids, such as bowel gas, may be expected in the abdomen for some patients. A quantity of expected or acceptable amount of bowel gas may be utilized in calculating the predetermined threshold. The optical images may also be analyzed to identify bulge in the surface of the patient to further confirm an internal gaseous void. In some examples, the extracted data regarding the presence of gaseous voids may be utilized in determining values of the different compartments based on the amount of gas or air detected.

Figure 8:
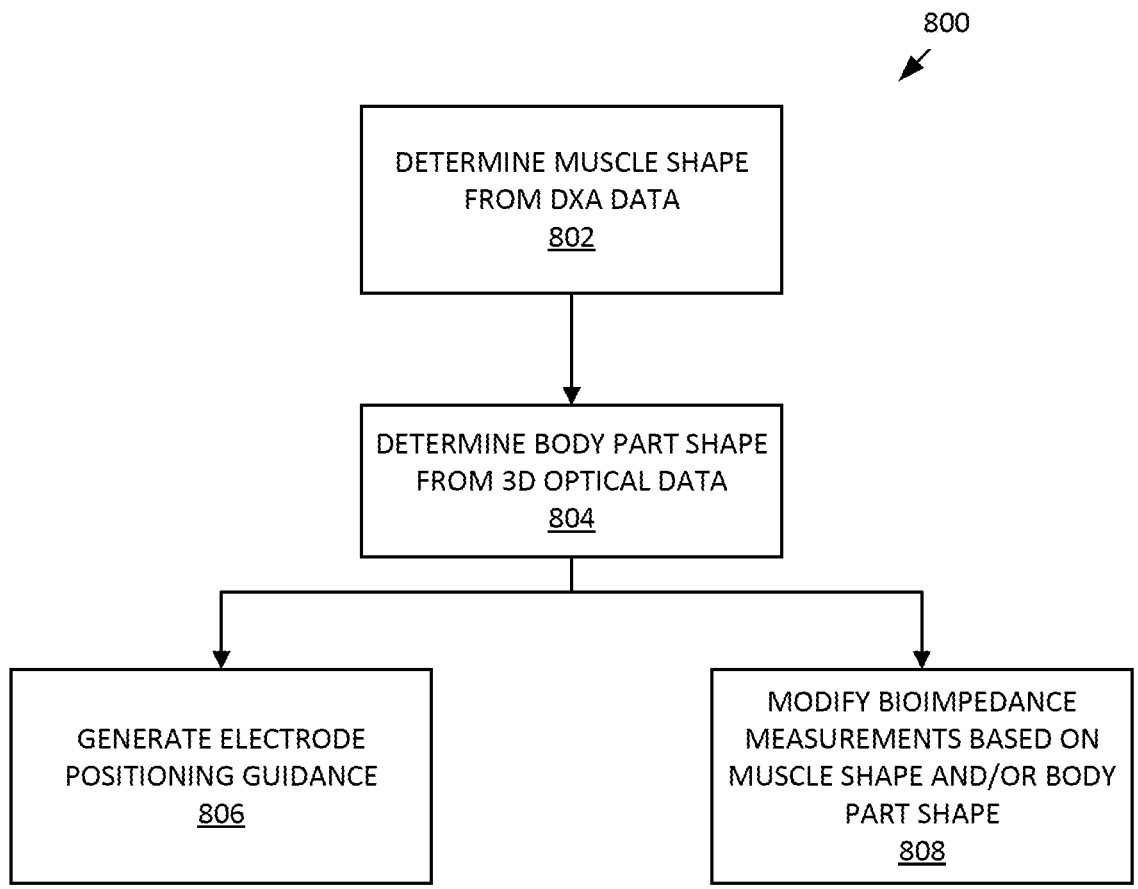
FIG. 8 depicts a method for modifying segmented bioimpedance measurements based on 3D optical and/or DXA data in accordance with an embodiment of the technology.

FIG. 8 depicts a method 800 for modifying segmented bioimpedance measurements based on 3D optical and/or DXA data in accordance with an embodiment of the technology. Bioimpedance analysis measurements are traditionally based on a set of assumptions based on the shape or geometry of the body, such as a geometry constant ($K_B$). One example of how a bioimpedance analysis is based on a geometry factor ($K_B$) is set forth in De Lorenzo A, Andreoli A, Matthie J, Withers P. Predicting body cell mass with bioimpedance by using theoretical methods: a technological review. J Appl Physiol 1997; 82:1542-58, which is incorporated by reference herein in its entirety. As described in Appendix C of the De Lorenzo reference, the geometry factor ($K_B$) is based on the geometry of five cylinders representing the volume of the body. By discerning the actual shape of the human body or muscle shapes of the body through DXA data and/or optical data, the five cylinder assumption can be improved. For example, the derivation of the geometry factor ($K_B$) can be based on an infinite number of cylinders having infinitesimal length, providing for an equation for the geometry factor ($K_B$) to be an integral for the circumference of the muscle for segments of the body, such as the arms, legs, and trunk. Method 800 provides solutions for improving segmented bioimpedance analysis for use with DXA data.

At operation 802, the shape of the muscle tissue for a desired body part is determined from the DXA data. The shape of the muscle may be determined from an image formed from the DXA data. At operation 804, the shape of the body portion may be determined from the 3D optical data captured by the 3D optical devices. For instance, the shape of a patient's arm may be determined from the 3D model of the patient, such as the 3D model generated in operation 506 of method 500 depicted in FIG. 5.

Based on either or both of the muscle shape determined in operation 802 and the body part shape data determined in operation 804, electrode positioning guidance for the bioimpedance analysis may be provided in operation 806. The location of the electrodes for a bioimpedance measurement may be a significant factor in accurately measuring a desired body part. By knowing the shape of the body part and/or the shape of the muscle through which the electrical signal will travel, the electrodes may be positioned in a more optimal manner. The guidance may be provided through a display screen with indicators displayed on an image of the patient or on a model of the patient.

The bioimpedance measurements may also be modified in operation 808 based on either or both of the muscle shape determined in operation 802 and the body part shape data determined in operation 804. As an example, the assumptions and/or approximations generally used in a bioimpedance analysis may be modified based on the actual shape of the muscle and/or the actual shape of the body part. For instance, in some bioimpedance analyses, an arm or leg may be approximated as a cylinder. By having the actual shape of the arm based on a 3D model of the patient, the actual shape may be used for the bioimpedance calculations rather than the cylindrical approximation. The actual shape of the muscle may be similarly used to further modify and refine the bioimpedance calculations. Further, the determined body part shape and/or muscle shape may be used to modify a boundary line used for segmenting and processing the DXA data.

In some examples, the DXA data and/or 3D optical data may be processed by the bioimpedance machine at the conclusion of the scan. Once the DXA data and/or 3D optical data is received and processed by the bioimpedance machine, the bioimpedance measurements may be taken. In other examples, the bioimpedance measurements may be taken prior to the DXA data and/or 3D optical data being processed, and those bioimpedance measurements may be modified at a later time once the DXA data and/or 3D optical data has been processed.

Figure 9:
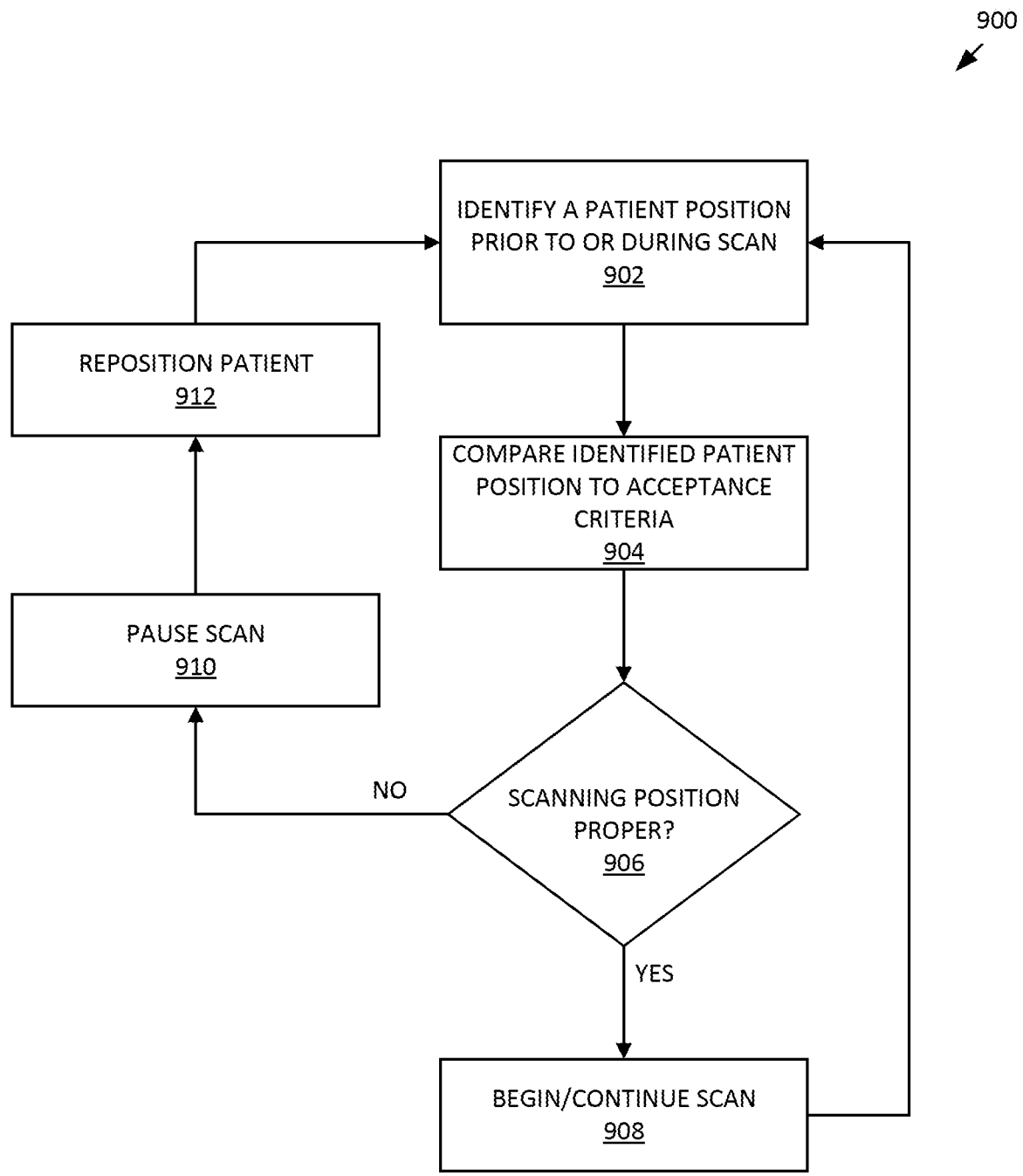
FIG. 9 depicts a method for confirming positioning of a target for scanning in accordance with an embodiment of the technology.

FIG. 9 depicts a method 900 for confirming positioning of a patient for scanning in accordance with an embodiment of the technology. At operation 902, a position of the patient is identified based on captured 3D optical images. The position of the patient may be identified either prior to a scan of the patient or during the scan. The patient position is then compared to acceptance criteria in operation 904. The acceptance criteria may include a plurality of rules or predefined acceptable positions. For instance, one rule may be that the entire patient must be entirely within the scanning field. Another rule may be that no portion of the patient is overlapping another portions of the patient. For instance, a patient may cross his or her legs or place his or her hands underneath another portion of the body, both of which would lead to inaccurate scan results. A determination as to whether the patient position satisfies the acceptance criteria and is therefore proper is made at operation 906. If the patient position is not proper, method 900 flows to operation 910 where the scanning of the patient is prevented from starting or paused if the scan has already been initiated. Upon pausing the scan, an alert may be presented to indicate an improper patient position. The alert may also display a reason as to why the patient position is improper along with instructions to provide to the patient to instruct the patient how to move to a proper position. At operation 912, the patient is repositioned into a proper position for subsequent scanning. The method 900 then flows back to operation 902 where the method 900 is repeated throughout the duration of the scan, either continuously or in intervals.

If the scanning position is determined to be proper in operation 906, the method 900 flows to operation 908 where the scan begins or continues if the scan has already been initiated. The method 900 then flows back to operation 902 where the method 900 is repeated throughout the duration of the scan, either continuously or in intervals. By continuing to confirm a proper position of the patient through 3D optical imaging, radiation exposure of the patient is limited to times where the patient is in a proper position. For instance, the emission of radiation is prevented when the patient is in an improper positon that would result in unusable or inaccurate scan data.

The examples described herein can be employed using software, hardware, or a combination of software and hardware to implement and perform the systems and methods disclosed herein. Although specific devices have been recited throughout the disclosure as performing specific functions, one of skill in the art will appreciate that these devices are provided for illustrative purposes, and other devices can be employed to perform the functionality disclosed herein without departing from the scope of the disclosure.

This disclosure described some examples of the present technology with reference to the accompanying drawings, in which only some of the possible examples were shown. Other aspects can, however, be embodied in many different forms and should not be construed as limited to the examples set forth herein. Rather, these examples were provided so that this disclosure was thorough and complete and fully conveyed the scope of the possible examples to those skilled in the art.

Although specific examples were described herein, the scope of the technology is not limited to those specific examples. One skilled in the art will recognize other examples or improvements that are within the scope of the present technology. Therefore, the specific structure, acts, or media are disclosed only as illustrative examples. Examples according to the invention may also combine elements or components of those that are disclosed in general but not expressly exemplified in combination, unless otherwise stated herein. The scope of the technology is defined by the following claims and any equivalents therein.

What is claimed is:

1. A system comprising:
a support structure configured to move along an axis of a scanning target;
a dual-energy x-ray source mounted to the support structure, the dual energy x-ray source configured to emit dual-energy x-rays towards the scanning target along a scan path;
an x-ray detector configured to detect the dual-energy x-rays emitted from the dual-energy x-ray source after passing through the scanning target;
a first 3D optical imaging device mounted to the support structure and configured to obtain a first 3D optical image of a first side of the scanning target along the scan path; and
a second 3D optical imaging device mounted to the support structure and configured to concurrently obtain a second 3D optical image of a second side of the scanning target, the second side being opposite the first side with respect to the scanning target; and
a processing device communicatively coupled to the x-ray detector and the first 3D optical imaging device;
wherein at least the first 3D optical imaging device and the second 3D optical imaging device are fixed in place with respect to the scanning target to capture surfaces of the scanning target to form a 3D model of the scanning target; and
the processing device is configured to determine, on a per-pixel basis, amounts of at least three of: bone, fat tissue, lean tissue, dehydrated lean tissue, and water.

2. The system of claim 1, further comprising an optically translucent patient support table or wall on which the scanning target is positioned, wherein the optically translucent table is disposed between the dual energy x-ray source and the detector.

3. The system of claim 1, further comprising a scale to measure the weight of the scanning target.

4. The system of claim 3, wherein the x-ray source is configured to move along the support structure in a direction transverse to the longitudinal axis of the scanning target.

5. The system of claim 1, wherein:
the support structure has a first arm and a second arm, the first arm and the second arm disposed on opposite sides of a scanning target; and
the first 3D optical imaging device is mounted to the first arm.

6. The system of claim 1, wherein the first 3D optical imaging device is selected from a group consisting of a stereoscopic device, a laser scanning device, a structured light device, and a modulated light device.

7. The system of claim 1, wherein the processing device is configured to compute a thickness of the scanning target on a per pixel basis.

8. The system of claim 1, further comprising a bioimpedance analysis device mounted to a portion of the system and communicatively coupled to the processing device.

9. The system of claim 1, wherein the system is configured to scan a patient in a standing position.

10. A system comprising:
a dual-energy x-ray source configured to move vertically along a longitudinal axis of the scanning target, the dual energy x-ray source configured to emit dual-energy x-rays towards a first side of the scanning target;
an x-ray detector configured to move in a vertical scan path along the longitudinal axis of the scanning target and configured to detect the dual-energy x-rays emitted from the dual-energy x-ray source after passing through the scanning target;
a first 3D optical imaging device configured to obtain a first 3D optical image of the first side of the scanning target along the vertical scan path;
a second 3D optical imaging device configured to concurrently obtain a second 3D optical image of a second side of the scanning target along the vertical scan path, the second side being opposite the first side with respect to the scanning target; and
a processing device communicatively coupled to the x-ray detector and the first 3D optical imaging device;
wherein at least the first 3D optical imaging device and the second 3D optical imaging device are fixed in place with respect to the scanning target to capture surfaces of the scanning target to form a 3D model of the scanning target; and
the processing device is configured to determine, on a per-pixel basis, amounts of at least three of: bone, fat tissue, lean tissue, dehydrated lean tissue, and water.

11. The system of claim 10, further comprising a radiolucent, transparent wall disposed between the dual-energy x-ray source and the x-ray detector.

12. The system of claim 1, wherein the first 3D optical imaging device is configured to capture the 3D optical image within one second before or after the dual-energy x-rays are emitted towards the scanning target.

13. The system of claim 10, wherein the first 3D optical imaging device is configured to capture the optical image within one second before or after the dual-energy x-rays are emitted towards the scanning target.

14. The system of claim 1, wherein the first 3D optical imaging device is configured to capture a position and shape of a patient at the same time as information from the dual-energy x-rays is obtained.

15. The system of claim 10, wherein at least one of the first 3D optical imaging device and the second 3D optical imaging device is configured to capture a position and shape of a patient at the same time as information from the dual-energy x-rays is obtained.

16. A system comprising:
a support structure configured to move along an axis of a scanning target;
a dual-energy x-ray source mounted to the support structure, the dual energy x-ray source configured to emit dual-energy x-rays towards the scanning target along a scan path;
an x-ray detector configured to detect the dual-energy x-rays emitted from the dual-energy x-ray source after passing through the scanning target; and
at least one optical imaging device mounted to the support structure and configured to obtain an optical image of a first side of the scanning target along the scan path;
a bioimpedance analysis device mounted to a portion of the system and communicatively coupled to a processing device, wherein a position of electrodes of the bioimpedance analysis device is based on at least one of dual-energy x-ray data provided by the dual-energy x-ray source and optical data provided by the at least one optical imaging device; and
the processing device being communicatively coupled to the x-ray detector and the at least one optical imaging device and being configured to determine, on a per-pixel basis, amounts of at least three of: bone, fat tissue, lean tissue, dehydrated lean tissue, and water.

17. The system of claim 1, further comprising:
a third 3D optical imaging device mounted to the support structure and configured to obtain a third 3D optical image of the scanning target along the scan path;
wherein the third 3D optical image combined with the first 3D optical image and the second 3D optical image form the 3D model of the scanning target.

18. The system of claim 10, further comprising:
a third 3D optical imaging device mounted to the support structure and configured to obtain a third 3D optical image of the scanning target along the scan path;
wherein the third 3D optical image combined with the first 3D optical image and the second 3D optical image form the 3D model of the scanning target.

* * * * *